(12) United States Patent
Kang et al.

(10) Patent No.: US 8,742,138 B2
(45) Date of Patent: Jun. 3, 2014

(54) COMPOUNDS AS HYPOXIA MIMETICS, AND COMPOSITIONS AND USES THEREOF

(75) Inventors: Xinshan Kang, Beijing (CN); Wei Long, Beijing (CN); Cunbo Ma, Beijing (CN); Yanping Wang, Nanjing (CN); Hong Cao, Beijing (CN); Yinxiang Wang, Beijing (CN); Fenlai Tan, Beijing (CN); Yunyan Hu, Beijing (CN)

(73) Assignees: Betta Pharmaceuticals Co., Ltd., Hangzhou, Zhejiang (CN); Xinshan Kang, Beijing (CN)

( * ) Notice: Subject to any disclaimer, the term of this patent is extended or adjusted under 35 U.S.C. 154(b) by 0 days.

(21) Appl. No.: 13/384,097

(22) PCT Filed: Jul. 14, 2010

(86) PCT No.: PCT/CN2010/001057
§ 371 (c)(1),
(2), (4) Date: Mar. 26, 2012

(87) PCT Pub. No.: WO2011/006355
PCT Pub. Date: Jan. 20, 2011

(65) Prior Publication Data
US 2012/0172399 A1  Jul. 5, 2012

(30) Foreign Application Priority Data

Jul. 15, 2009 (CN) .......................... 2009 1 0089274

(51) Int. Cl.
*C07D 311/02* (2006.01)
(52) U.S. Cl.
USPC ......................................... 549/285
(58) Field of Classification Search
USPC ......................................... 549/285
See application file for complete search history.

(56) References Cited

U.S. PATENT DOCUMENTS 8,324,405 B2 * 12/2012 Ho et al. ...................... 549/285

FOREIGN PATENT DOCUMENTS

| WO | WO 03/080649 | 10/2003 |
| WO | WO 2007/070359 | 6/2007 |
| WO | WO 2008/119744 | 10/2008 |
| WO | WO 2009/100250 | 8/2009 |

OTHER PUBLICATIONS

Takechi et al. Chem.Phar.Bull., 2000, 48(11), 1702-1710.*
Bonsignore, et al., Heterocycles (1997), 45(11), 2131-2136.*
Wolff, Burger's medicinal Chemistry and Drug Discovery, vol. 1, Principles and Practice, John Wiley & sons, New York, 1997.*
West, Solid State Chemistry and Its Applications, John Wiley & Sons, 1984.*
Dorwald F. A. Side Reactions in Organic Synthesis, 2005, Wiley: VCH, Weinheim p. IX of Preface p. 1-15.*
Venkatesh et al., Role of the Development Scientist in Compound Lead Selection and Optimization J. Pharm. Sci. 89, 145-54 (2000).*
Takechi, Haruko et al. Screening search for organic fluorophores: syntheses and fluorescence properties of 3-azolyl-7-diethylaminocoumarin derivatives. Chemical & Pharmaceutical Bulletin, 2000, vol. 48, No. 11, pp. 1702-1710.

* cited by examiner

*Primary Examiner* — Nizal Chandrakumar
(74) *Attorney, Agent, or Firm* — Weisun Rao; Greenberg Traurig, LLP

(57) ABSTRACT

This invention relates to new compounds that can serve as hypoxia mimetics. This invention also relates to methods of increasing HIF levels or activity in a subject or treating a condition associated with HIF levels or activity in a subject by administering to the subject at least one of these compounds.

49 Claims, 2 Drawing Sheets

COMPOUNDS AS HYPOXIA MIMETICS, AND COMPOSITIONS AND USES THEREOF

CROSS REFERENCE TO RELATED APPLICATIONS

This application is a national phase application and claims the benefit, under 35 U.S.C. §371, of PCT/CN2010/001057, filed on Jul. 14, 2010, which in turn claims priority to CN 200910089274.1, filed on Jul. 15, 2009. Both applications are incorporated herein by reference in their entireties.

This application claims benefit of priority to Chinese priority patent application serial no. 200910089274.1 filed on Jul. 15, 2009, which is hereby incorporated by reference in its entirety.

FIELD OF THE INVENTION

The present invention relates to substituted heterocyclic compounds, and compositions thereof as well as methods of use the same as hypoxia mimetics. This invention further relates to methods of increasing HIF (Hypoxia Inducible Factor) levels or activity in a subject or treating a condition associated with HIF levels or activity such as ischemia, anemia, wound healing, auto-transplantation, allo-transplantation, xenotransplantation, systemic high blood pressure, thalassemia, diabetes, cancer, and an inflammatory disorder.

BACKGROUND OF THE INVENTION

The cellular transcription factor HIF (Hypoxia Inducible Factor) occupies a central position in oxygen homeostasis in a wide range of organisms and is a key regulator of responses to hypoxia. The genes regulated by HIF transcriptional activity can play critical roles in angiogenesis, erythropoiesis, hemoglobin F production, energy metabolism, inflammation, vasomotor function, apoptosis and cellular proliferation. HIF can also play a role in cancer, in which it is commonly upregulated, and in the pathophysiological responses to ischemia and hypoxia.

The HIF transcriptional complex comprises an heterodimer: HIF is a constitutive nuclear protein that dimerizes with oxygen-regulated HIF subunits. Oxygen regulation occurs through hydroxylation of the HIF subunits, which are then rapidly destroyed by the proteasome. In oxygenated cells, the von Hippel-Lindau tumor suppressor protein (pVHL) binds to hydroxylated HIF-subunits, thereby promoting their ubiquitin dependent proteolysis. This process is suppressed under hypoxic conditions, stabilizing HIF and promoting transcriptional activation by the HIF complex.

Hydroxylation of HIF-subunits can occur on proline and asparagine residues and can be mediated by a family of 2-oxoglutarate dependent enzymes. This family includes the HIF prolyl hydroxylase isozymes (PHDs), which hydroxylate Pro 402 and Pro 564 of human HIF1, as well as Factor Inhibiting HIF (FIH), which hydroxylates Asn 803 of human HIF1. Inhibition of FIB or the PHDs leads to HIF stabilization and transcriptional activation. See, e.g., Schofield and Ratcliffe, Nature Rev. Mol. Cell Biol., Vo 15, pages 343-354 (2004).

Thus, new or improved agents that modulate (such as increasing HIF levels or activity) HIF are continually needed for developing new and more effective pharmaceuticals to treat HIF-associated conditions or diseases or disorders, such as ischemia, anemia, wound healing, auto-transplantation, allo-transplantation, xenotransplantation, systemic high blood pressure, thalassemia, diabetes, cancer, and an inflammatory disorder, to name a few. In discovering new or improved agents that modulate HIF level or activity, it is also desirable but not required to discover agents with improved chemical or biological properties such as solubility, bioavailability, pharmacokinetics, pharmacodynamics, toxicity and/or less side effects such as less cardiovascular side effects. The compounds, compositions, and methods described herein are directed toward these needs and other ends.

SUMMARY OF THE INVENTION

The present invention provides, inter alia, compounds of Formula I:

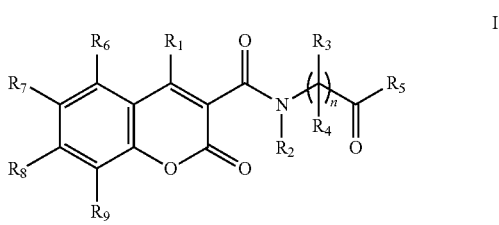

a pharmaceutically acceptable salt thereof, a solvate thereof, a chelate thereof, a non-covalent complex thereof, a prodrug thereof, or a mixture of any of the foregoing, wherein constituent members are provided below.

The present invention further provides pharmaceutical compositions comprising a compound of Formula I or pharmaceutically acceptable salt thereof, and at least one pharmaceutically acceptable carrier.

The present invention further provides methods of modulating an activity of HIF comprising contacting the HIF with a compound of Formula I or pharmaceutically acceptable salt of the same.

The present invention further provides methods of increasing an activity of HIF with a compound of Formula I or pharmaceutically acceptable salt of the same.

The present invention further provides methods of modulating (such as increasing) the level of HIF in a subject (such as a cell or a patient) comprising administering to the subject a therapeutically effective amount of a compound of Formula I or pharmaceutically acceptable salt of the same.

The present invention further provides methods of treating one or more of the various HIF-associated conditions, diseases, and disorders named herein by administering to a patient a therapeutically effective amount of a compound of Formula I or pharmaceutically acceptable salt of the same.

The present invention further provides compounds of Formula I or pharmaceutically acceptable salts thereof, for use in therapy.

The present invention further provides use of the compounds of Formula I or pharmaceutically acceptable salts thereof, for the manufacture/preparation of a medicament for use in therapy.

DETAILED DESCRIPTION

Figure 1:
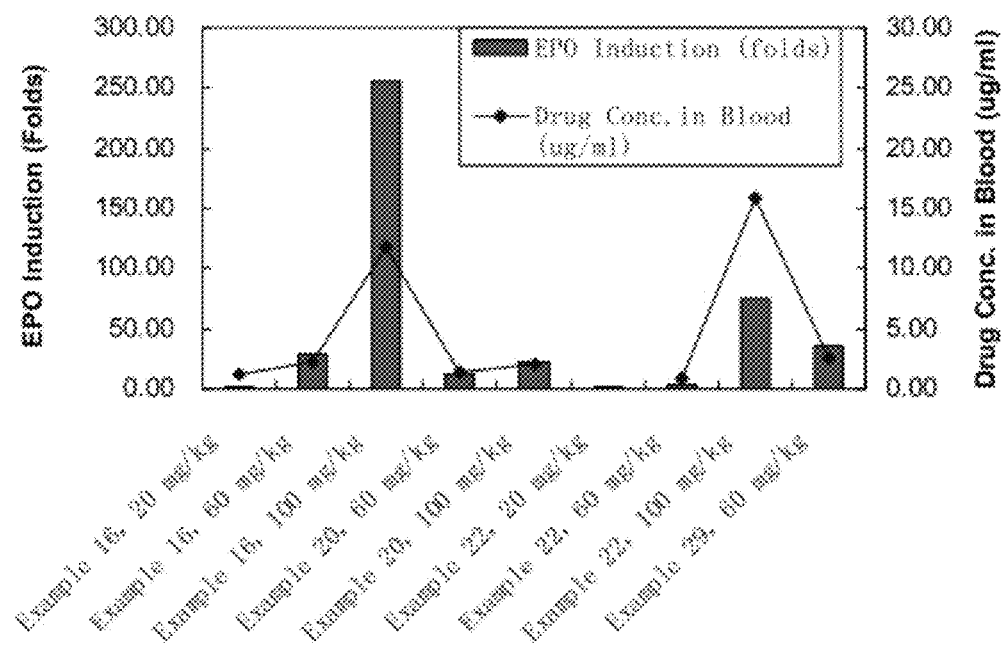
FIG. 1 illustrates certain example compounds' effects on the level of EPO in mice 4 hours after the administration of different compounds (using the assay described in Example B).
Figure 2:
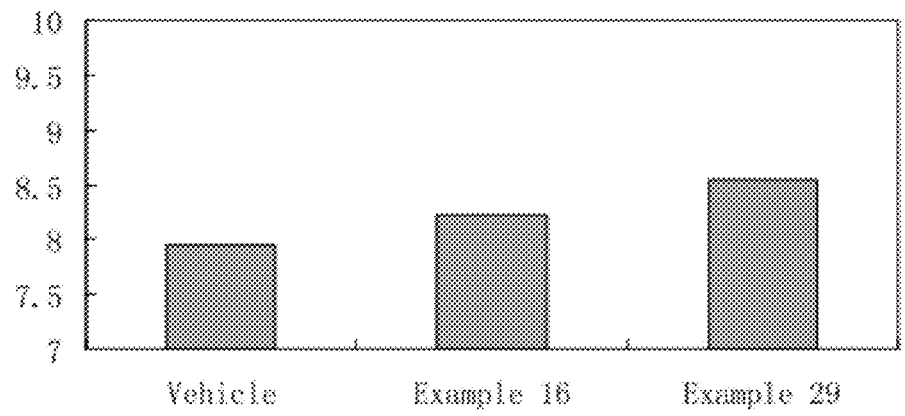
FIG. 2 illustrates certain example compounds' effects on the level of red blood cell counts (RBC) in mice at Day 9 after 7 days of daily dosage of 60 mg/kg (using the assay described in Example C).
Figure 3:
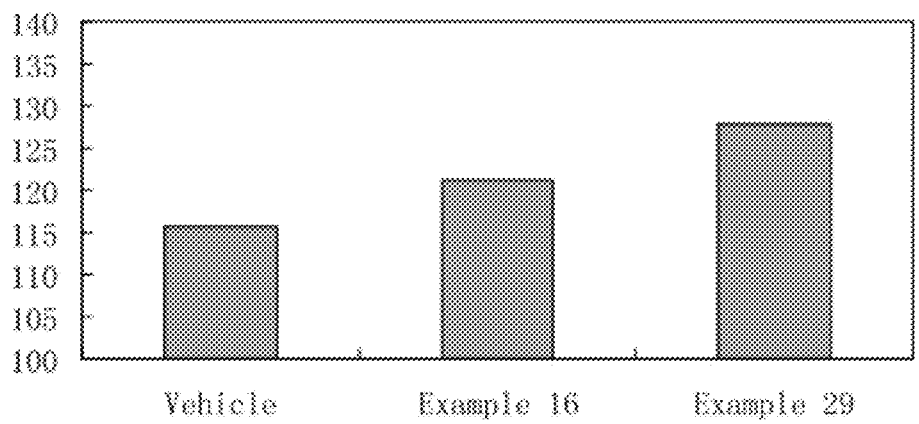
FIG. 3 illustrates certain example compounds' effects on the level of blood hemoglobin (HGB) in mice at Day 9 after 7 days of daily dosage of 60 mg/kg (using the assay described in Example C).
Figure 4:
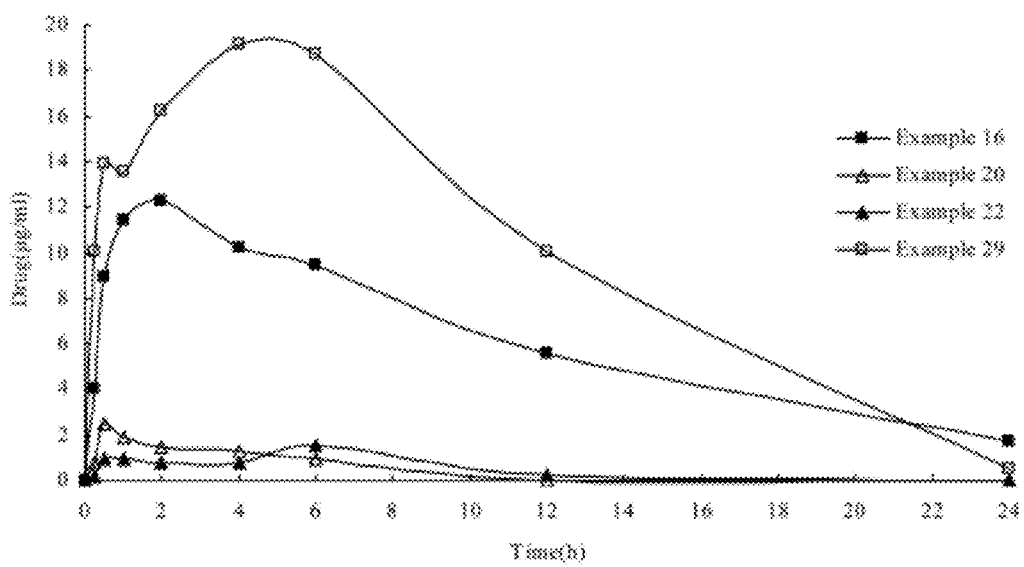
FIG. 4 illustrates the pharmacokinetic curves in rats for certain example compounds after single oral dosage of 50 mg/kg (using the assay described in Example D).

The present invention provides, inter alia, compounds of Formula I:

a pharmaceutically acceptable salt thereof, a solvate thereof, a chelate thereof, a non-covalent complex thereof, a prodrug thereof, and mixtures of any of the foregoing, wherein:

n is 1 to 6;

$R_1$ is selected from OH, SH, $NR_3R_4$, $NHC(O)R_2$, $NHSO_2R_2$ and sulfonyl;

$R_2$ is selected from H, lower alkyl and substituted lower alkyl;

$R_3$ and $R_4$ are independently selected from H, lower alkyl, substituted lower alkyl, lower haloalkyl, substituted lower haloalkyl, or $R_3$ and $R_4$ can join together to form a 3 to 6 membered ring or a substituted 3 to 6 membered ring;

$R_5$ is selected from OH, SH, $NH_2$, lower alkyl, substituted lower alkyl, lower alkoxy, substituted lower alkoxy, and sulfanyl;

each of $R_6$, $R_7$, $R_8$ and $R_9$ is independently selected from H, alkyl, substituted alkyl, alkenyl, substituted alkenyl, alkynyl, substituted alkynyl, alkoxy, substituted alkoxy, $NR_3R_4$, C(O)OH, $OR_{12}$, $SR_{12}$, $SO_2R_{12}$, CN, $NO_2$, halogen, aryl, substituted aryl, heteroaryl, substituted heteroaryl, arylalkyl, substituted arylalkyl, heteroarylalkyl, substituted heteroarylalkyl, heterocycloalkyl, substituted heterocycloalkyl, alkylsilyl, substituted alkylsilyl, alkenylsilyl, substituted alkenylsilyl, alkynylsilyl, substituted alkynylsilyl, alkoxycarbonyl, substituted alkoxycarbonyl, and —X—$R_{11}$;

or at least one of adjacent pairs $R_1$ and $R_6$, $R_6$ and $R_7$, $R_7$ and $R_8$, and $R_8$ and $R_9$, can join together to form a 4 to 7 membered ring or a substituted 4 to 7 membered ring;

X is selected from —N($R_{10}$)—Y— and —Y—N($R_{10}$)—;

Y is selected from C(O), $SO_2$, alkylene, substituted alkylene, alkenylene, substituted alkenylene, alkynylene, and substituted alkynylene;

$R_{10}$ is selected from H, lower alkyl, and substituted lower alkyl;

$R_{11}$ is selected from H, cycloalkyl, substituted cycloalkyl, heterocycloalkyl, substituted heterocycloalkyl, aryl, substituted aryl, heteroaryl, and substituted heteroaryl; and $R_{12}$ is selected from H, alkyl, substituted alkyl, alkenyl, substituted alkenyl, alkynyl, substituted alkynyl and $NR_3R_4$.

In some embodiments, $R_1$ is selected from OH and SH. In some further embodiments, $R_1$ is OH.

In some embodiments, $R_2$ is selected from H and lower alkyl (such as methyl or ethyl). In some further embodiments, $R_2$ is H.

In some embodiments, $R_3$ and $R_4$ are each, independently, selected from H, lower alkyl, and lower haloalkyl. In some embodiments, $R_3$ and $R_4$ are each, independently, selected from H and lower alkyl (such as methyl or ethyl). In some embodiments, $R_3$ and $R_4$ are each H.

In some embodiments, $R_3$ and $R_4$, together with the carbon atom to which they are attached, can form a 3 to 6 membered cycloalkyl or heterocycloalkyl ring, wherein the 3 to 6 membered cycloalkyl or heterocycloalkyl ring is optionally substituted with 1, 2, 3, 4, or 5 substituents each independently selected from lower alkyl, lower alkoxy, lower haloalkyl, lower haloalkoxy, halogen, and OH. In some further embodiments, $R_3$ and $R_4$, together with the carbon atom to which they are attached, form a 3 to 6 membered cycloalkyl optionally substituted with 1, 2, 3, 4, or 5 substituents each independently selected from lower alkyl, lower alkoxy, lower haloalkyl, lower haloalkoxy, halogen, and OH. In some further embodiments, $R_3$ and $R_4$, together with the carbon atom to which they are attached, form a 3 to 6 membered cycloalkyl which is unsubstituted.

In some embodiments, $R_3$ and $R_4$, together with the carbon atom to which they are attached, form a 3 to 6 membered heterocycloalkyl optionally substituted with 1, 2, 3, 4, or 5 substituents each independently selected from lower alkyl, lower alkoxy, lower haloalkyl, lower haloalkoxy, halogen, and OH. In some further embodiments, the heterocycloalkyl formed by $R_3$ and $R_4$, together with the carbon atom to which they are attached comprises at least one or two heteroatoms each independently selected from O, S, and N. In some further embodiments, $R_3$ and $R_4$, together with the carbon atom to which they are attached, form a 3 to 6 membered heterocycloalkyl selected from pyrrolidinyl, piperidinyl, tetrahydrofuranyl, and tetrahydropyranyl.

In some embodiments, $R_5$ is selected from OH, SH, $NH_2$, and lower alkoxy. In some further embodiments, $R_5$ is selected from OH and SH. In yet further embodiments, $R_5$ is OH.

In some embodiments, $R_5$ is selected from OH, $NH_2$, and lower alkoxy (such as methoxy, ethoxy and propoxy).

In some embodiments, $R_5$ is selected from OH, lower alkoxy (such as methoxy, ethoxy and propoxy), and substituted lower alkoxy.

In some embodiments, at least one of adjacent pairs $R_6$ and $R_7$, $R_7$ and $R_8$, and $R_8$ and $R_9$, can join together (and together with the two carbon atoms to which they are attached) to form a 4 to 7 membered ring or a substituted 4 to 7 membered ring. In some further embodiments, the 4 to 7 membered ring or the substituted 4 to 7 membered ring comprises at least one, two, or three heteroatoms.

In some embodiments, $R_6$ and $R_7$ are each, independently, selected from H, halogen, OH, lower alkyl, lower haloalkyl, lower alkoxy, lower haloalkoxy. In some further embodiments, $R_6$ and $R_7$ are each, independently, selected from H, halogen, lower alkyl (such as methyl or ethyl), and lower haloalkyl (such as trifluoromethyl). In yet embodiments, $R_6$ and $R_7$ are each H.

In some embodiments, $R_8$ and $R_9$ are each, independently, selected from H, halogen, OH, lower alkyl, lower haloalkyl, lower alkoxy, lower haloalkoxy. In some further embodiments, $R_8$ and $R_9$ are each, independently, selected from H, halogen, lower alkyl (such as methyl or ethyl), and lower haloalkyl (such as trifluoromethyl). In yet embodiments, $R_8$ and $R_9$ are each H.

In some embodiments, at least one of $R_6$, $R_7$, $R_8$ and $R_9$ is independently selected from halo, haloalkyl and haloalkoxy.

In some embodiments, at least one of $R_6$, $R_7$, $R_8$ and $R_9$ is independently selected from alkoxy or substituted alkoxy.

In some embodiments, at least one of $R_6$, $R_7$, $R_8$ and $R_9$ is independently selected from alkylsilyl, substituted alkylsilyl, alkynylsilyl, and substituted alkynylsilyl.

In some embodiments, at least one of $R_6$, $R_7$, $R_8$ and $R_9$ is independently selected from aryl, substituted aryl, heteroaryl, substituted heteroaryl, heterocycloalkyl, and substituted heterocycloalkyl.

In some embodiments, at least one of $R_6$, $R_7$, $R_8$ and $R_9$ is independently selected from H, alkyl, substituted alkyl, alkenyl, substituted alkenyl, alkynyl, and substituted alkynyl.

In some embodiments, at least one of $R_8$ and $R_9$ is heteroaryl or substituted heteroaryl. In some further embodiments, at least one of $R_8$ and $R_9$ is heteroaryl selected from pyridyl (e.g., 2-pyridyl, 3-pyridyl, or 4-pyridyl), thienyl, furanyl. In yet further embodiments, at least one of $R_8$ and $R_9$ is heteroaryl selected from pyridyl (e.g., 2-pyridyl, 3-pyridyl, or 4-pyridyl).

In some embodiments, at least one of $R_8$ and $R_9$ is independently selected from substituted aryl, and substituted heteroaryl.

In some embodiments, at least one of $R_8$ and $R_9$ is independently selected from substituted phenyl, and substituted pyridyl.

In some embodiments, at least one of $R_8$ and $R_9$ is phenyl substituted with halogen, alkyl, haloalkyl, alkoxy, and haloalkoxy at the para- or meta-position. In some further embodiments, one of $R_8$ and $R_9$ is phenyl substituted with halogen, alkyl, haloalkyl, alkoxy, and haloalkoxy at the para- or meta-position; and the other of $R_8$ and $R_9$ is H, halogen, OH, lower alkyl, lower haloalkyl, lower alkoxy, lower haloalkoxy. In yet further embodiments, one of $R_8$ and $R_9$ is phenyl substituted with halogen, alkyl, haloalkyl, alkoxy, and haloalkoxy at the para- or meta-position; and the other of $R_8$ and $R_9$ is H.

In some embodiments, at least one of $R_8$ and $R_9$ is pyridyl substituted with halogen, alkyl, haloalkyl, alkoxy, and haloalkoxy at the para- or meta-position. In some further embodiments, one of $R_8$ and $R_9$ is pyridyl substituted with halogen, alkyl, haloalkyl, alkoxy, and haloalkoxy at the para- or meta-position; and the other of $R_8$ and $R_9$ is H, halogen, OH, lower alkyl, lower haloalkyl, lower alkoxy, lower haloalkoxy. In yet further embodiments, one of $R_8$ and $R_9$ is pyridyl substituted with halogen, alkyl, haloalkyl, alkoxy, and haloalkoxy at the para- or meta-position; and the other of $R_8$ and $R_9$ is H.

In some embodiments, n is 1, 2, or 3. In some further embodiments, n is 1 or 2. In yet further embodiments, n is 1.

In some embodiments, the compound of Formula I or pharmaceutically acceptable salt thereof is a compound of Formula II:

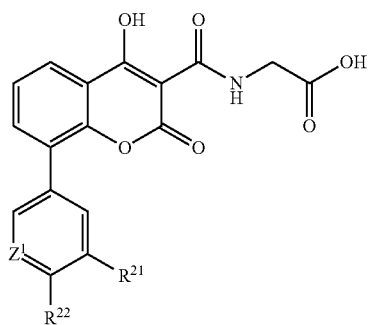

II or pharmaceutically acceptable salt thereof, wherein:
$R^{21}$ is selected from H, halogen, lower alkyl, lower haloalkyl, lower alkoxy, and lower haloalkoxy;

$R^{22}$ is selected from H, halogen, lower alkyl, lower haloalkyl, lower alkoxy, and lower haloalkoxy;

$Z^1$ is N or $CR^{23}$; and $R^{23}$ is selected from H, halogen, lower alkyl, lower haloalkyl, lower alkoxy, and lower haloalkoxy;

provided that at least one of $R^{21}$ and $R^{22}$ and $R^{23}$ (if present) is selected from halogen, lower alkyl, lower haloalkyl, lower alkoxy, and lower haloalkoxy.

In some embodiments of compound of Formula II or pharmaceutically acceptable salt thereof, $R^{21}$ is selected from H, Cl, F, methyl, ethyl, trifluoromethyl, methoxy, ethoxy, and trifluoromethoxy.

In some embodiments of compound of Formula II or pharmaceutically acceptable salt thereof, $R^{22}$ is selected from H, Cl, F, methyl, ethyl, trifluoromethyl, methoxy, ethoxy, and trifluoromethoxy.

In some embodiments of compound of Formula II or pharmaceutically acceptable salt thereof, $Z^1$ is N.

In some embodiments of compound of Formula II or pharmaceutically acceptable salt thereof, $Z^1$ is $CR^{23}$.

In some embodiments of compound of Formula II or pharmaceutically acceptable salt thereof, $Z^1$ is $CR^{23}$ and $R^{23}$ is selected from H, Cl, F, methyl, ethyl, trifluoromethyl, methoxy, ethoxy, and trifluoromethoxy.

In some embodiments of compound of Formula II or pharmaceutically acceptable salt thereof, $Z^1$ is $CR^{23}$; one of $R^{21}$, $R^{22}$, and $R^{23}$ is selected from halogen, lower alkyl, lower haloalkyl, lower alkoxy, and lower haloalkoxy; and the other two of $R^{21}$, $R^{22}$, and $R^{23}$ are both H.

In some embodiments of compound of Formula II or pharmaceutically acceptable salt thereof, $Z^1$ is $CR^{23}$; one of $R^{21}$ and $R^{23}$ is selected from halogen, lower alkyl, lower haloalkyl, lower alkoxy, and lower haloalkoxy; and the other one of $R^{21}$ and $R^{23}$ is H. In some further embodiments, $R^{22}$ is H.

In some embodiments of compound of Formula II or pharmaceutically acceptable salt thereof, $Z^1$ is $CR^{23}$; two of $R^{21}$, $R^{22}$, and $R^{23}$ are each independently selected from halogen, lower alkyl, lower haloalkyl, lower alkoxy, and lower haloalkoxy; and the other one of $R^{21}$, $R^{22}$, and $R^{23}$ is H. In some further embodiments, $R^{23}$ is H. In other further embodiments, $R^{22}$ is H.

In some embodiments of compound of Formula II or pharmaceutically acceptable salt thereof, $Z^1$ is $CR^{23}$; $R^{21}$, $R^{22}$, and $R^{23}$ are each independently selected from halogen, lower alkyl, lower haloalkyl, lower alkoxy, and lower haloalkoxy.

In some embodiments of compound of Formula II or pharmaceutically acceptable salt thereof, $Z^1$ is N; one of $R^{21}$ and $R^{22}$ is selected from halogen, lower alkyl, lower haloalkyl, lower alkoxy, and lower haloalkoxy; and the other of $R^{21}$ and $R^{22}$ is H.

In some embodiments of compound of Formula II or pharmaceutically acceptable salt thereof, $Z^1$ is N; $R^{21}$ and $R^{22}$ are each independently selected from halogen, lower alkyl, lower haloalkyl, lower alkoxy, and lower haloalkoxy.

In some embodiments, the compound of Formula II or pharmaceutically acceptable salt thereof is a compound of Formula IIa

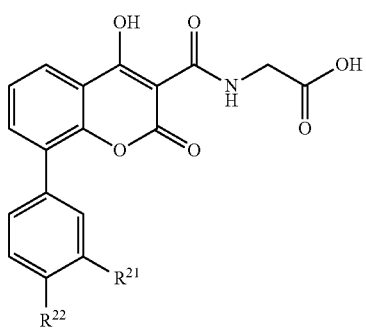

or pharmaceutically acceptable salt thereof, wherein:

$R^{21}$ is selected from H, halogen, lower alkyl, lower haloalkyl, lower alkoxy, and lower haloalkoxy; and $R^{22}$ is selected from H, halogen, lower alkyl, lower haloalkyl, lower alkoxy, and lower haloalkoxy;

provided that at least one of $R^{21}$ and $R^{22}$ is selected from halogen, lower alkyl, lower haloalkyl, lower alkoxy, and lower haloalkoxy.

In some embodiments of compound of Formula IIa or pharmaceutically acceptable salt thereof, $R^{21}$ is H; and $R^{22}$ is selected from halogen, lower alkyl, lower haloalkyl, lower alkoxy, and lower haloalkoxy.

In some embodiments of compound of Formula IIa or pharmaceutically acceptable salt thereof, $R^{21}$ is H; and $R^{22}$ is selected from lower alkyl and lower haloalkyl.

In some embodiments of compound of Formula IIa or pharmaceutically acceptable salt thereof, $R^{21}$ is H; and $R^{22}$ is selected from $C_{1-3}$ alkyl and $C_{1-3}$ haloalkyl. In some further embodiments, $R^{22}$ is selected from $C_{1-2}$ alkyl and $C_{1-2}$ haloalkyl. In yet further embodiments, $R^{22}$ is selected from methyl and $C_1$ haloalkyl.

In some embodiments of compound of Formula IIa or pharmaceutically acceptable salt thereof, $R^{21}$ is H; and $R^{22}$ is selected from $C_{1-3}$ alkyl. In some further embodiments, $R^{22}$ is selected from methyl or ethyl. In yet further embodiments, $R^{22}$ is methyl.

In some embodiments of compound of Formula IIa or pharmaceutically acceptable salt thereof, $R^{22}$ is H; and $R^{21}$ is selected from halogen, lower alkyl, lower haloalkyl, lower alkoxy, and lower haloalkoxy.

In some embodiments of compound of Formula IIa or pharmaceutically acceptable salt thereof, $R^{22}$ is H; and $R^{21}$ is selected from lower alkyl and lower haloalkyl.

In some embodiments of compound of Formula IIa or pharmaceutically acceptable salt thereof, $R^{22}$ is H; and $R^{21}$ is selected from $C_{1-3}$ alkyl and $C_{1-3}$ haloalkyl. In some further embodiments, $R^{21}$ is selected from $C_{1-2}$ alkyl and $C_{1-2}$ haloalkyl. In yet further embodiments, $R^{21}$ is selected from methyl and $C_1$ haloalkyl.

In some embodiments of compound of Formula IIa or pharmaceutically acceptable salt thereof, $R^{22}$ is H; and $R^{21}$ is selected from $C_{1-3}$ alkyl. In some further embodiments, $R^{21}$ is selected from methyl or ethyl. In yet further embodiments, $R^{21}$ is methyl.

In some embodiments of compound of Formula IIa or pharmaceutically acceptable salt thereof, $R^{21}$ and $R^{22}$ are each independently selected from halogen, lower alkyl, lower haloalkyl, lower alkoxy, and lower haloalkoxy.

In some embodiments of compound of Formula IIa or pharmaceutically acceptable salt thereof, $R^{21}$ and $R^{22}$ are each independently selected from lower alkyl and lower haloalkyl.

In some embodiments of compound of Formula IIa or pharmaceutically acceptable salt thereof, $R^{21}$ and $R^{22}$ are each independently selected from $C_{1-3}$ alkyl and $C_{1-3}$ haloalkyl. In some further embodiments, $R^{21}$ and $R^{22}$ are each independently selected from $C_{1-2}$ alkyl and $C_{1-2}$ haloalkyl. In yet further embodiments, $R^{21}$ and $R^{22}$ are each independently selected from methyl and $C_1$ haloalkyl.

In some embodiments of compound of Formula IIa or pharmaceutically acceptable salt thereof, $R^{21}$ and $R^{22}$ are each independently selected from $C_{1-3}$ alkyl. In some further embodiments, $R^{21}$ and $R^{22}$ are each independently selected from methyl or ethyl. In yet further embodiments, $R^{21}$ and $R^{22}$ are each methyl.

In some embodiments, the compound of Formula I or pharmaceutically acceptable salt thereof is a compound of Formula III:

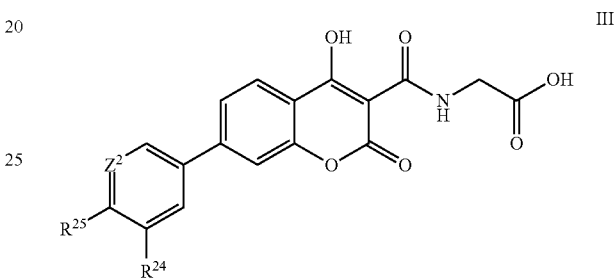

or pharmaceutically acceptable salt thereof, wherein:

$R^{24}$ is selected from H, halogen, lower alkyl, lower haloalkyl, lower alkoxy, and lower haloalkoxy;

$R^{25}$ is selected from H, halogen, lower alkyl, lower haloalkyl, lower alkoxy, and lower haloalkoxy;

$Z^2$ is N or $CR^{26}$; and $R^{26}$ is selected from H, halogen, lower alkyl, lower haloalkyl, lower alkoxy, and lower haloalkoxy;

provided that at least one of $R^{24}$ and $R^{25}$ and $R^{26}$ (if present) is selected from halogen, lower alkyl, lower haloalkyl, lower alkoxy, and lower haloalkoxy.

In some embodiments of compound of Formula III or pharmaceutically acceptable salt thereof, $R^{24}$ is selected from H, Cl, F, methyl, ethyl, trifluoromethyl, methoxy, ethoxy, and trifluoromethoxy.

In some embodiments of compound of Formula III or pharmaceutically acceptable salt thereof, $R^{25}$ is selected from H, Cl, F, methyl, ethyl, trifluoromethyl, methoxy, ethoxy, and trifluoromethoxy.

In some embodiments of compound of Formula III or pharmaceutically acceptable salt thereof, $Z^2$ is N.

In some embodiments of compound of Formula III or pharmaceutically acceptable salt thereof, $Z^2$ is $CR^{26}$.

In some embodiments of compound of Formula III or pharmaceutically acceptable salt thereof, $Z^2$ is $CR^{26}$ and $R^{26}$ is selected from H, Cl, F, methyl, ethyl, trifluoromethyl, methoxy, ethoxy, and trifluoromethoxy.

In some embodiments of compound of Formula III or pharmaceutically acceptable salt thereof, $Z^2$ is $CR^{26}$; one of $R^{24}$, $R^{25}$, and $R^{26}$ is selected from halogen, lower alkyl, lower haloalkyl, lower alkoxy, and lower haloalkoxy; and the other two of $R^{24}$, $R^{25}$, and $R^{26}$ are both H.

In some embodiments of compound of Formula III or pharmaceutically acceptable salt thereof, $Z^2$ is $CR^{26}$; one of $R^{24}$ and $R^{26}$ is selected from halogen, lower alkyl, lower haloalkyl, lower alkoxy, and lower haloalkoxy; and the other one of $R^{24}$ and $R^{26}$ is H. In some further embodiments, $R^{25}$ is H.

In some embodiments of compound of Formula III or pharmaceutically acceptable salt thereof, $Z^2$ is $CR^{26}$; two of $R^{24}$, $R^{25}$, and $R^{26}$ are each independently selected from halogen, lower alkyl, lower haloalkyl, lower alkoxy, and lower haloalkoxy; and the other one of $R^{24}$, $R^{25}$, and $R^{26}$ is H. In some further embodiments, $R^{26}$ is H. In other further embodiments, $R^{25}$ is H.

In some embodiments of compound of Formula III or pharmaceutically acceptable salt thereof, $Z^1$ is $CR^{26}$; $R^{24}$, $R^{25}$, and $R^{26}$ are each independently selected from halogen, lower alkyl, lower haloalkyl, lower alkoxy, and lower haloalkoxy.

In some embodiments of compound of Formula III or pharmaceutically acceptable salt thereof, $Z^1$ is N; one of $R^{24}$ and $R^{25}$ is selected from halogen, lower alkyl, lower haloalkyl, lower alkoxy, and lower haloalkoxy; and the other of $R^{24}$ and $R^{25}$ is H.

In some embodiments of compound of Formula III or pharmaceutically acceptable salt thereof, $Z^1$ is N; $R^{24}$ and $R^{25}$ are each independently selected from halogen, lower alkyl, lower haloalkyl, lower alkoxy, and lower haloalkoxy.

In some embodiments, the compound of Formula III or pharmaceutically acceptable salt thereof is a compound of Formula IIIa

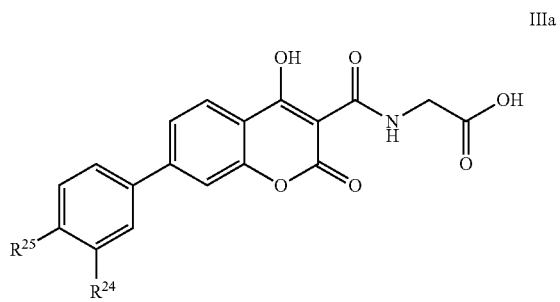

IIIa or pharmaceutically acceptable salt thereof, wherein:
$R^{24}$ is selected from H, halogen, lower alkyl, lower haloalkyl, lower alkoxy, and lower haloalkoxy; and
$R^{25}$ is selected from H, halogen, lower alkyl, lower haloalkyl, lower alkoxy, and lower haloalkoxy;
provided that at least one of $R^{24}$ and $R^{25}$ is selected from halogen, lower alkyl, lower haloalkyl, lower alkoxy, and lower haloalkoxy.

In some embodiments of compound of Formula IIIa or pharmaceutically acceptable salt thereof, $R^{24}$ is H; and $R^{25}$ is selected from halogen, lower alkyl, lower haloalkyl, lower alkoxy, and lower haloalkoxy.

In some embodiments of compound of Formula IIIa or pharmaceutically acceptable salt thereof, $R^{24}$ is H; and $R^{25}$ is selected from lower alkyl and lower haloalkyl.

In some embodiments of compound of Formula IIIa or pharmaceutically acceptable salt thereof, $R^{24}$ is H; and $R^{25}$ is selected from $C_{1-3}$ alkyl and $C_{1-3}$ haloalkyl. In some further embodiments, $R^{25}$ is selected from $C_{1-2}$ alkyl and $C_{1-2}$ haloalkyl. In yet further embodiments, $R^{25}$ is selected from methyl and $C_1$ haloalkyl.

In some embodiments of compound of Formula IIIa or pharmaceutically acceptable salt thereof, $R^{24}$ is H; and $R^{25}$ is selected from $C_{1-3}$ alkyl. In some further embodiments, $R^{25}$ is selected from methyl or ethyl. In yet further embodiments, $R^{25}$ is methyl.

In some embodiments of compound of Formula IIIa or pharmaceutically acceptable salt thereof, $R^{25}$ is H; and $R^{24}$ is selected from halogen, lower alkyl, lower haloalkyl, lower alkoxy, and lower haloalkoxy.

In some embodiments of compound of Formula IIIa or pharmaceutically acceptable salt thereof, $R^{25}$ is H; and $R^{24}$ is selected from lower alkyl and lower haloalkyl.

In some embodiments of compound of Formula IIIa or pharmaceutically acceptable salt thereof, $R^{25}$ is H; and $R^{24}$ is selected from $C_{1-3}$ alkyl and $C_{1-3}$ haloalkyl. In some further embodiments, $R^{24}$ is selected from $C_{1-2}$ alkyl and $C_{1-2}$ haloalkyl. In yet further embodiments, $R^{24}$ is selected from methyl and $C_1$ haloalkyl.

In some embodiments of compound of Formula IIIa or pharmaceutically acceptable salt thereof, $R^{25}$ is H; and $R^{24}$ is selected from $C_{1-3}$ alkyl. In some further embodiments, $R^{24}$ is selected from methyl or ethyl. In yet further embodiments, $R^{24}$ is methyl.

In some embodiments of compound of Formula IIIa or pharmaceutically acceptable salt thereof, $R^{24}$ and $R^{25}$ are each independently selected from halogen, lower alkyl, lower haloalkyl, lower alkoxy, and lower haloalkoxy.

In some embodiments of compound of Formula IIIa or pharmaceutically acceptable salt thereof, $R^{24}$ and $R^{25}$ are each independently selected from lower alkyl and lower haloalkyl.

In some embodiments of compound of Formula IIIa or pharmaceutically acceptable salt thereof, $R^{24}$ and $R^{25}$ are each independently selected from $C_{1-3}$ alkyl and $C_{1-3}$ haloalkyl. In some further embodiments, $R^{24}$ and $R^{25}$ are each independently selected from $C_{1-2}$ alkyl and $C_{1-2}$ haloalkyl. In yet further embodiments, $R^{24}$ and $R^{25}$ are each independently selected from methyl and $C_1$ haloalkyl.

In some embodiments of compound of Formula IIIa or pharmaceutically acceptable salt thereof, $R^{24}$ and $R^{25}$ are each independently selected from $C_{1-3}$ alkyl. In some further embodiments, $R^{24}$ and $R^{25}$ are each independently selected from methyl or ethyl. In yet further embodiments, $R^{24}$ and $R^{25}$ are each methyl.

Also provided herein is a pharmaceutical composition comprising at least one pharmaceutically acceptable excipient, adjuvant, or carrier, and a therapeutically effective amount of at least one compound described herein.

Further provided are pharmaceutical compositions comprising at least one pharmaceutically acceptable excipient, adjuvant, or carrier, and a therapeutically effective amount of at least one compound described herein in combination with at least one additional compound such as an erythropoiesis stimulating agent or chemotherapeutic agent.

Additionally provided herein is a method of by administering to the subject at least one compound described herein or pharmaceutically acceptable salt thereof, or use of a compound described herein or pharmaceutically acceptable salt thereof in the manufacturing a medicament for, modulating (such as increasing) HIF levels or activity in a subject.

Further provided is a method of by administering to the subject at least one compound described herein or pharmaceutically acceptable salt thereof, or use of a compound described herein or pharmaceutically acceptable salt thereof in the manufacturing a medicament for, treating a condition where it is desired to modulate HIF activity comprising administering to a subject at least one compound described herein.

Also provided is a method of by administering to the subject at least one compound described herein or pharmaceutically acceptable salt thereof, or use of a compound described herein or pharmaceutically acceptable salt thereof in the manufacturing a medicament for, treating a anemic or ischemic related disorder in a subject comprising administering to a subject at least one compound described herein.

Also provided is a method of by administering to the subject at least one compound described herein or pharmaceutically acceptable salt thereof, or use of a compound described herein or pharmaceutically acceptable salt thereof in the manufacturing a medicament for, treating ischemia, anemia, wound healing, auto-transplantation, allo-transplantation, xeno-transplantation, systemic high blood pressure, thalassemia, diabetes, cancer or an inflammatory disorder, or a combination of two or more thereof in a subject comprising administering to a subject at least one compound described herein.

Also provided is a method of by administering to the subject at least one compound described herein or pharmaceutically acceptable salt thereof, or use of a compound described herein or pharmaceutically acceptable salt thereof in the manufacturing a medicament for, treating anemia in a subject comprising administering to a subject at least one compound described herein.

Further provided is a method of by administering to the subject at least one compound described herein or pharmaceutically acceptable salt thereof, or use of a compound described herein or pharmaceutically acceptable salt thereof in the manufacturing a medicament for, modulating the amount of HIF in a cell comprising contacting the cell with at least one compound described herein.

Additionally provided is a method of by administering to the subject at least one compound described herein or pharmaceutically acceptable salt thereof, or use of a compound described herein or pharmaceutically acceptable salt thereof in the manufacturing a medicament for, increasing the amount of hemoglobin F in a subject comprising administering to the subject at least one compound described herein.

Also provided is a method of by administering to the subject at least one compound described herein or pharmaceutically acceptable salt thereof, or use of a compound described herein or pharmaceutically acceptable salt thereof in the manufacturing a medicament for, modulating angiogenesis in a subject comprising administering to the subject at least one compound described herein.

Additionally provided is a method of by administering to the subject at least one compound described herein or pharmaceutically acceptable salt thereof, or use of a compound described herein or pharmaceutically acceptable salt thereof in the manufacturing a medicament for, treating at least one disease in a patient in need of such treatment comprising administering to the patient a therapeutically effective amount of at least one compound described herein.

Also provided is a method of by administering to the subject at least one compound described herein or pharmaceutically acceptable salt thereof, or use of a compound described herein or pharmaceutically acceptable salt thereof in the manufacturing a medicament for, inhibiting HIF hydroxylation in a subject comprising administering to the subject at least one compound described herein.

Additional embodiments of the invention are set forth in the description which follows, or may be learned by practice of the invention.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, when any variable occurs more than one time in a chemical formula, its definition on each occurrence is independent of its definition at every other occurrence. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

Compounds of Formula I, II, IIa, III and IIIa include, but are not limited to optical isomers of compounds of Formula I, II, IIa, III and IIIa, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I, II, IIa, III and IIIa include Z- and E-forms (or cis- and trans-forms) of compounds with double bonds. Where compounds of Formula I, II, IIa, III and IIIa exists in various tautomeric forms, chemical entities of the present invention include all tautomeric forms of the compound.

Compounds of the present disclosure include, but are not limited to compounds of Formula I and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used henceforth, the term "compound" encompasses not only the compound itself, but also a pharmaceutically acceptable salt thereof, a solvate thereof, a chelate thereof, a non-covalent complex thereof, a prodrug thereof, and mixtures of any of the foregoing.

As noted above, prodrugs also fall within the scope of chemical entities, for example, ester or amide derivatives of the compounds of Formula I, II, IIa, III and IIIa. The term "prodrugs" includes any compounds that become compounds of Formula I, II, IIa, III and IIIa when administered to a patient, e.g., upon metabolic processing of the prodrug. Examples of prodrugs include, but are not limited to, acetate, formate, and benzoate and like derivatives of functional groups (such as alcohol oramine groups) in the compounds of Formula I, II, IIa, III and IIIa.

The term "solvate" refers to the compound formed by the interaction of a solvent and a compound. Suitable solvates are pharmaceutically acceptable solvates, such as hydrates, including monohydrates and hemi-hydrates.

At various places in the present specification, substituents of compounds of the invention are disclosed in groups or in ranges. It is specifically intended that the invention include each and every individual subcombination of the members of such groups and ranges. For example, the term "$C_{1-3}$ alkyl" is specifically intended to individually disclosed methyl, ethyl, and $C_3$ alkyl (including n-propryl and isopropyl).

For compounds of the invention in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, pyridine is an example of a 6-membered heteroaryl ring and thiophene is an example of a 5-membered heteroaryl group.

"Alkyl" refers to a saturated, branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. In certain embodiments, an alkyl group comprises from 1 to 20 carbon atoms. As used herein the term "lower alkyl" refers to an alkyl group comprising from 1 to 6 carbon atoms.

"Alkenyl" refers to an unsaturated branched, straight-chain or cyclic alkyl group having at least one carbon-carbon double bond derived by the removal of one hydrogen atom from a single carbon atom of a parent alkene. The group may be in either the Z- or E-forms (or cis or trans conformation) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. In certain embodiments, an alkenyl group has from 2 to 20 carbon atoms and in other embodiments, from 2 to 6 carbon atoms, i.e. "lower alkenyl."

"Alkynyl" refers to an unsaturated branched or straight-chain having at least one carbon-carbon triple bond derived by the removal of one hydrogen atom from a single carbon atom of a parent alkyne. Typical alkynyl groups include, but are not limited to, ethynyl; propynyl; butynyl, 2-pentynyl, 3-pentynyl, 2-hexynyl, 3-hexynyl and the like. In certain embodiments, an alkynyl group has from 2 to 20 carbon atoms and in other embodiments, from 2 to 6 carbon atoms (i.e. "lower alkynyl").

"Alkoxy" refers to a radical —OR where R represents an alkyl. Representative examples include, but are not limited to, methoxy, ethoxy, propoxy, butoxy, cyclohexyloxy, and the like.

"Alkoxycarbonyl" refers to a radical —C(O)—OR where R represents an alkyl as defined herein.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. For example, aryl includes 5- and 6-membered carbocyclic aromatic rings fused to a 5- to 7-membered heterocycloalkyl ring containing 1 or more heteroatoms selected from N, O, and S. In certain embodiments, an aryl group can comprise from 6 to 10 carbon atoms. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

"Arylalkyl" or "aralkyl" refers to an acyclic alkyl group in which one of the hydrogen atoms bonded to a carbon atom, typically a terminal or sp3 carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkyl, arylalkenyl, and/or arylalkynyl is used. In certain embodiments, an arylalkyl group can be ($C_{6-30}$) arylalkyl, e.g., the alkyl group of the arylalkyl group can be ($C_{1-10}$) and the aryl moiety can be ($C_{5-20}$).

"Carbonyl" refers to a radical —C(O) group.

"Carboxy" refers to the radical —C(O)OH.

"Cyano" refers to the radical —CN.

"Cycloalkyl" refers to a saturated or unsaturated, but non-aromatic, cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In certain embodiments, the cycloalkyl group can be $C_{3-10}$ cycloalkyl, such as, for example, $C_{3-6}$ cycloalkyl.

"Heterocycloalkyl" refers to a saturated or unsaturated, but non-aromatic, cyclic alkyl group in which one or more carbon atoms (and any associated hydrogen atoms) are independently replaced with the same or different heteroatom and its associated hydrogen atoms, where appropriate. Typical heteroatoms to replace the carbon atom(s) include, but are not limited to, N, P, O, S, and Si. Where a specific level of saturation is intended, the nomenclature "heterocycloalkanyl" or "heterocycloalkenyl" is used. Typical heterocycloalkyl groups include, but are not limited to, groups derived from epoxides, imidazolidine, morpholine, piperazine, piperidine, pyrazolidine, pyrrolidine, quinuclidine, tetrahydrofuran, tetrahydropyran and the like. Substituted heterocycloalkyl also includes ring systems substituted with one or more oxo (=O) or oxide (—O$^-$) substituents, such as piperidinyl N-oxide, morpholinyl-N-oxide, 1-oxo-1-thiomorpholinyl and 1,1-dioxo-1-thiomorpholinyl.

"Disease" refers to any disease, disorder, condition, symptom, or indication.

"Halo" refers to a fluoro, chloro, bromo, or iodo group.

"Heteroaryl" refers to a monovalent heteroaromatic group derived by the removal of one hydrogen atom from a single atom of a parent heteroaromatic ring system. Heteroaryl encompasses: 5- to 7-membered aromatic, monocyclic rings containing one or more, for example, from 1 to 4, or in certain embodiments, from 1 to 3, heteroatoms selected from N, O, and S, with the remaining ring atoms being carbon; and polycyclic heterocycloalkyl rings containing one or more, for example, from 1 to 4, or in certain embodiments, from 1 to 3, heteroatoms selected from N, O, and S, with the remaining ring atoms being carbon and wherein at least one heteroatom is present in an aromatic ring.

For example, heteroaryl includes a 5- to 7-membered heteroaromatic ring fused to a 5- to 7-membered cycloalkyl ring and a 5- to 7-membered heteroaromatic ring fused to a 5- to 7-membered heterocycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perirnidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, oxazole, and pyrazine.

"Heteroarylalkyl" or "heteroaralkyl" refers to an acyclic alkyl group in which one of the hydrogen atoms bonded to a carbon atom, typically a terminal or sp3 carbon atom, is replaced with a heteroaryl group. Where specific alkyl moieties are intended, the nomenclature heteroarylalkanyl, heteroarylalkenyl, and/or heteroarylalkynyl is used. In certain embodiments, the heteroarylalkyl group can be a 6 to 30 membered heteroarylalkyl, e.g., the alkanyl, alkenyl or alkynyl moiety of the heteroarylalkyl can be 1 to 10 membered and the heteroaryl moiety can be a 5 to 20-membered heteroaryl.

"Sulfonyl" refers to a radical —S(O)$_2$R where R is an alkyl, substituted alkyl, substituted cycloalkyl, substituted heterocycloalkyl, substituted aryl, or substituted heteroaryl group as defined herein. Representative examples include, but are not limited to methylsulfonyl, ethylsulfonyl, propylsulfonyl, butylsulfonyl, and the like.

"Sulfanyl" refers to a radical —SR where R is an alkyl, substituted alkyl, substituted cycloalkyl, substituted heterocycloalkyl, substituted aryl, or substituted heteroaryl group as defined herein that may be optionally substituted as defined herein. Representative examples include, but are not limited to, methylthio, ethylthio, propylthio, butylthio, and the like.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered.

"Pharmaceutically acceptable vehicle" refers to any of a diluent, adjuvant, excipient or carrier with which at least one compound of the present disclosure is administered.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereoisomers."

"Subject" includes mammals and humans. The terms "human" and "subject" are used interchangeably herein.

"Substituted" refers to a group in which one or more hydrogen atoms are each independently replaced with the same or different substituent(s). Typical substituents include, but are not limited to, —X, —R$_{33}$, —OH, =O, —OR$_{33}$, SR$_{33}$, —SH, =S, —NR$_{33}$R$_{34}$, —NR$_{33}$, —CX$_3$, —CF$_3$, —CN, —NO$_2$, —S(O)$_2$R$_{33}$, —OS(O$_2$)OH, —OS(O)$_2$R$_{33}$, —OP(O)(OR$_{33}$)(OR$_{34}$), —C(O)R$_{33}$, —C(S)R$_{33}$, —C(O)OR$_{33}$, —C(O)NR$_{33}$R$_{34}$, —C(O)OH, —C(S)OR$_{33}$, —NR$_{35}$C(O)NR$_{33}$R$_{34}$, —NR$_{35}$C(S)NR$_{33}$R$_{34}$, —NR$_{35}$C(NR$_{33}$)NR$_{33}$R$_{34}$, —C(NR$_{33}$)NR$_{33}$R$_{34}$, —S(O)$_2$NR$_{33}$R$_{34}$, —NR$_{35}$S(O)$_2$R$_{33}$, —NR$_{35}$C(O)R$_{33}$, and S(O)R$_{33}$ where each X is independently a halo; each R$_{33}$ and R$_{34}$ are independently hydrogen, alkyl, substituted alkyl, aryl, substituted aryl, arylalkyl, substituted arylalkyl, cycloalkyl, substituted cycloalkyl, heterocycloalkyl, substituted heterocycloalkyl, heteroaryl, substituted heteroaryl, heteroarylalkyl, substituted heteroarylalkyl, —NR$_{35}$R$_{36}$, —C(O)R$_{35}$ or —S(O)$_2$R$_{35}$ or optionally R$_{33}$ and R$_{34}$ together with the atom to which R$_{33}$ and R$_{34}$ are attached form one or more heterocycloalkyl, substituted heterocycloalkyl, heteroaryl, or substituted heteroaryl rings; and R$_{35}$ and R$_{36}$ are independently hydrogen, alkyl, substituted alkyl, aryl, substituted aryl, arylalkyl, substituted arylalkyl, cycloalkyl, substituted cycloalkyl, heterocycloalkyl, substituted heterocycloalkyl, heteroaryl, substituted heteroaryl, heteroarylalkyl or substituted heteroarylalkyl, or optionally R$_{35}$ and R$_{36}$ together with the nitrogen atom to which R$_{35}$ and R$_{36}$ are attached form one or more heterocycloalkyl, substituted heterocycloalkyl, heteroaryl, or substituted heteroaryl rings. In certain embodiments, a tertiary amine or aromatic nitrogen may be substituted with one or more oxygen atoms to form the corresponding nitrogen oxide.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Certain embodiments of the present invention are directed to at least one compound of Formula I:

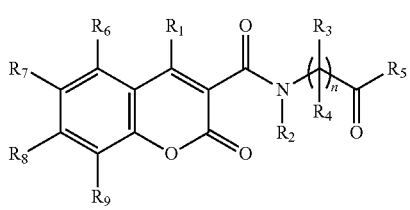

I a pharmaceutically acceptable salt thereof, a solvate thereof, a chelate thereof, a non-covalent complex thereof, a prodrug thereof, and mixtures of any of the foregoing, wherein:

n is 1 to 6;

$R_1$ is selected from OH, SH, $NR_3R_4$, $NHC(O)R_2$, $NHSO_2R_2$ and sulfonyl;

$R_2$ is selected from H, lower alkyl and substituted lower alkyl;

$R_3$ and $R_4$ are independently selected from H, lower alkyl, substituted lower alkyl, lower haloalkyl, substituted lower haloalkyl, or $R_3$ and $R_4$ can join together to form a 3 to 6 membered ring or a substituted 3 to 6 membered ring;

$R_5$ is selected from OH, SH, $NH_2$, lower alkyl, substituted lower alkyl, lower alkoxy, substituted lower alkoxy, and sulfanyl;

each of $R_6$, $R_7$, $R_8$ and $R_9$ is independently selected from H, alkyl, substituted alkyl, alkenyl, substituted alkenyl, alkynyl, substituted alkynyl, alkoxy, substituted alkoxy, $NR_3R_4$, C(O)OH, $OR_{12}$, $SR_{12}$, $SO_2R_{12}$, CN, $NO_2$, halogen, aryl, substituted aryl, heteroaryl, substituted heteroaryl, arylalkyl, substituted arylalkyl, heteroarylalkyl, substituted heteroarylalkyl, heterocycloalkyl, substituted heterocycloalkyl, alkylsilyl, substituted alkylsilyl, alkenylsilyl, substituted alkenylsilyl, alkynylsilyl, substituted alkynylsilyl, alkoxycarbonyl, substituted alkoxycarbonyl, and —X—$R_{11}$;

or at least one of adjacent pairs $R_1$ and $R_6$, $R_6$ and $R_7$, $R_7$ and $R_8$, and $R_8$ and $R_9$, can join together to form a 4 to 7 membered ring or a substituted 4 to 7 membered ring;

X is selected from —N($R_{10}$)—Y— and —Y—N($R_{10}$)—;

Y is selected from C(O), $SO_2$, alkylene, substituted alkylene, alkenylene, substituted alkenylene, alkynylene, and substituted alkynylene;

$R_{10}$ is selected from H, lower alkyl, and substituted lower alkyl, $R_{11}$ is selected from H, cycloalkyl, substituted cycloalkyl, heterocycloalkyl, substituted heterocycloalkyl, aryl, substituted aryl, heteroaryl, and substituted heteroaryl; and $R_{12}$ is selected from H, alkyl, substituted alkyl, alkenyl, substituted alkenyl, alkynyl, substituted alkynyl and $NR_3R_4$.

In certain embodiments of compounds of Formula I, $R_1$ is selected from OH and SH.

In certain embodiments of compounds of Formula I, $R_2$ is H.

In certain embodiments of compounds of Formula I, $R_3$ and $R_4$ are each independently selected from H, lower alkyl such as methyl or ethyl, and substituted lower alkyl (such as lower alkyl substituted with hydroxyl, for example hydroxymethyl).

In certain embodiments of compounds of Formula I, $R_5$ is selected from OH, a lower alkoxy such as methoxy, ethoxy and propoxy, and a substituted lower alkoxy.

In certain embodiments of compounds of Formula I, $R_3$ and $R_4$ join together to form a 3 to 6 membered ring or a substituted 3 to 6 membered ring. The 3 to 6 membered rings can comprise at least one heteroatom, such as at least two heteroatoms.

In certain embodiments of compounds of Formula I, $R_1$ and $R_6$ can join together to form a 4 to 7 membered ring or a substituted 4 to 7 membered ring. The 4 to 7 membered rings can comprise at least one heteroatom, such as at least two heteroatoms, and at least three heteroatoms.

In certain embodiments of compounds of Formula I, at least one of $R_6$, $R_7$, $R_8$ and $R_9$ is independently selected from halo and a moiety substituted with at least one halogen, such as trifluoromethyl.

In certain embodiments of compounds of Formula I, at least one of $R_6$, $R_7$, $R_8$ and $R_9$ is independently selected from alkoxy or substituted alkoxy.

In certain embodiments of compounds of Formula I, at least one of $R_6$, $R_7$, $R_8$ and $R_9$ is independently selected from alkylsilyl, substituted alkylsilyl, alkynylsilyl, and substituted alkynylsilyl.

In certain embodiments of compounds of Formula I, at least one of $R_6$, $R_7$, $R_8$ and $R_9$ is independently selected from aryl, substituted aryl, heteroaryl, substituted heteroaryl, heterocycloalkyl, and substituted heterocycloalkyl, such as substituted pyridines, substituted pyrimidines, substituted pyrazines, substituted pyridazines, substituted tetrahydrofurans, and substituted piperidines.

In certain embodiments of compounds of Formula I, at least one of $R_6$, $R_7$, $R_8$ and $R_9$ is independently selected from H, alkyl, substituted alkyl, alkenyl, substituted alkenyl, alkynyl, and substituted alkynyl, such as isopropyl, cyclohexane, cyclopentane, cyclohexene and cyclopentene.

Examples of individual representative compounds of the present disclosure, and compounds comprised in compositions of the present disclosure, and used in methods of the present disclosure are listed in Table 1. Each compound listed in Table 1, i.e., Examples 1-38, contains information directed to its structure, name, molecular weight, hydrogen NMR data and at least one method of synthesis.

In certain embodiments, compounds of the present disclosure inhibit prolyl hydroxylases such as HIF prolyl hydroxylases. Variety of assays may be used to determine the prolyl hydroxylase inhibitory activity of a compound.

In certain embodiments, compounds of the present disclosure modulate HIF levels or activity, for example, by stabilizing HIF.

Furthermore, compounds of the present disclosure can contain one or more chiral centers. Such compounds can be prepared or isolated as pure stereoisomers, i.e., as individual enantiomers or diastereomers, or as stereoisomer-enriched mixtures. All such stereoisomers, and enriched mixtures thereof, are included within the scope of the present disclosure. Pure stereoisomers, and enriched mixtures thereof, can be prepared using, for example, optically active starting materials or stereoselective reagents well-known in the art. Alternatively, racemic mixtures of such compounds can be separated using, for example, chiral column chromatography, chiral resolving agents and the like.

Certain embodiments of the present disclosure are directed to a pharmaceutical composition comprising at least one pharmaceutically acceptable excipient, adjuvant or carrier, and a therapeutically effective amount of at least one compound described herein. The at least one compound can be present in an amount effective for the treatment of at least one disease selected from ischemia, anemia, wound healing, auto-transplantation, allo-transplantation, xeno-transplantation, systemic high blood pressure, thalassemia, diabetes, cancer and an inflammatory disorder.

Other embodiments of the present disclosure are directed to a method of treating a condition where it is desired to modulate HIF activity comprising administering to a subject at least one compound described herein. The condition can be selected from at least one of ischemia, anemia, wound healing, auto-transplantation, allo-transplantation, xenotransplantation, systemic high blood pressure, thalassemia, diabetes, cancer and an inflammatory disorder.

A further embodiment is directed to a method of treating at least one disease in a patient in need of such treatment comprising administering to the patient a therapeutically effective amount of at least one compound described herein. The at least one disease can be selected from ischemia, anemia, wound healing, auto-transplantation, allo-transplantation, xeno-transplantation, systemic high blood pressure, thalassemia, diabetes, cancer and an inflammatory disorder.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

The compounds of invention can be prepared, for example, according to one or more of the following general reaction schemes and techniques described below.

General Scheme I

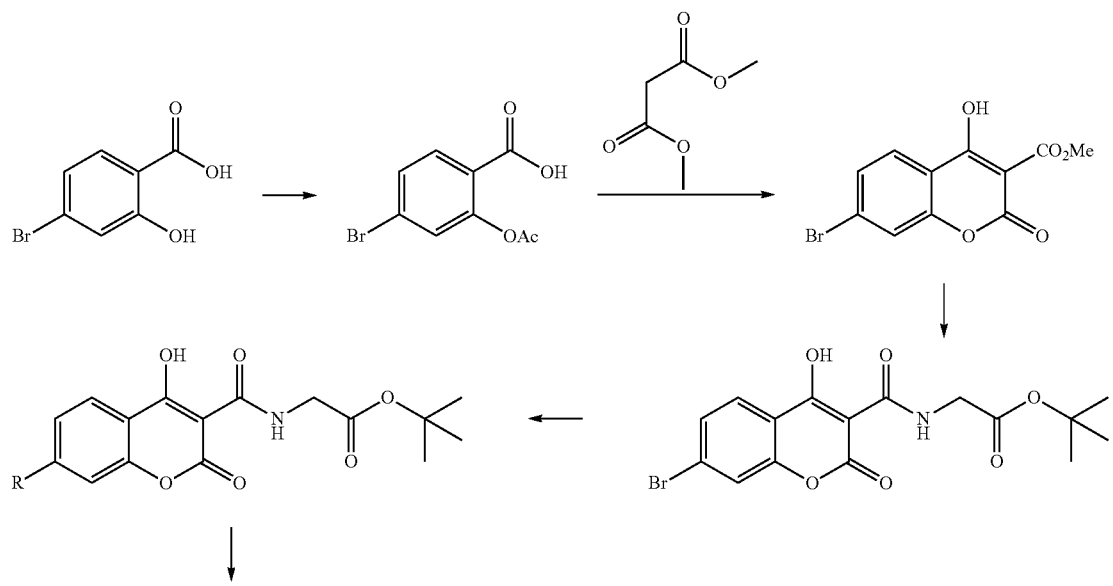

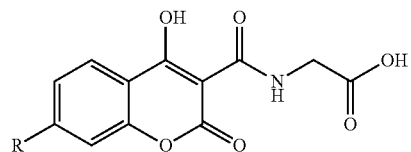
-continued
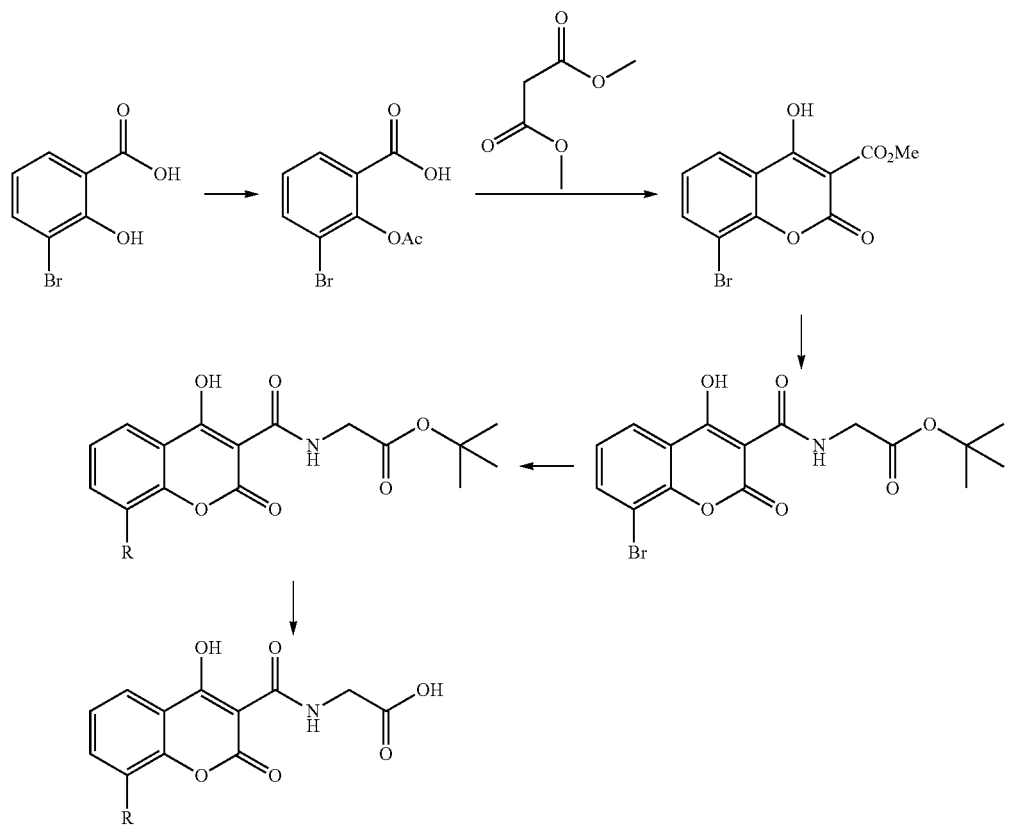
General Scheme II
EXAMPLES
The present invention is further exemplified, but not limited, by the following examples that illustrate the preparation of compounds of Formulas I, II, IIa, III, or IIIa, according to the invention.
Example 1
Synthesis of N-[(4-hydroxy-2-oxo-7-phenyl-2H-3-chromenyl)carbonyl]glycine
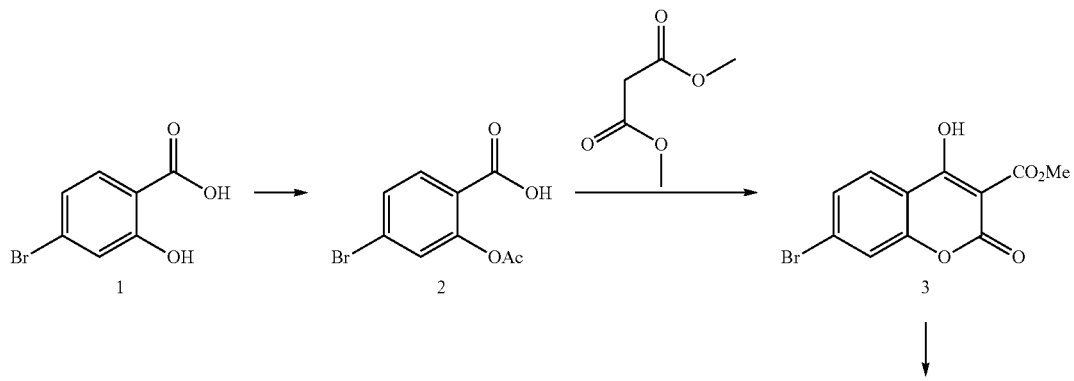

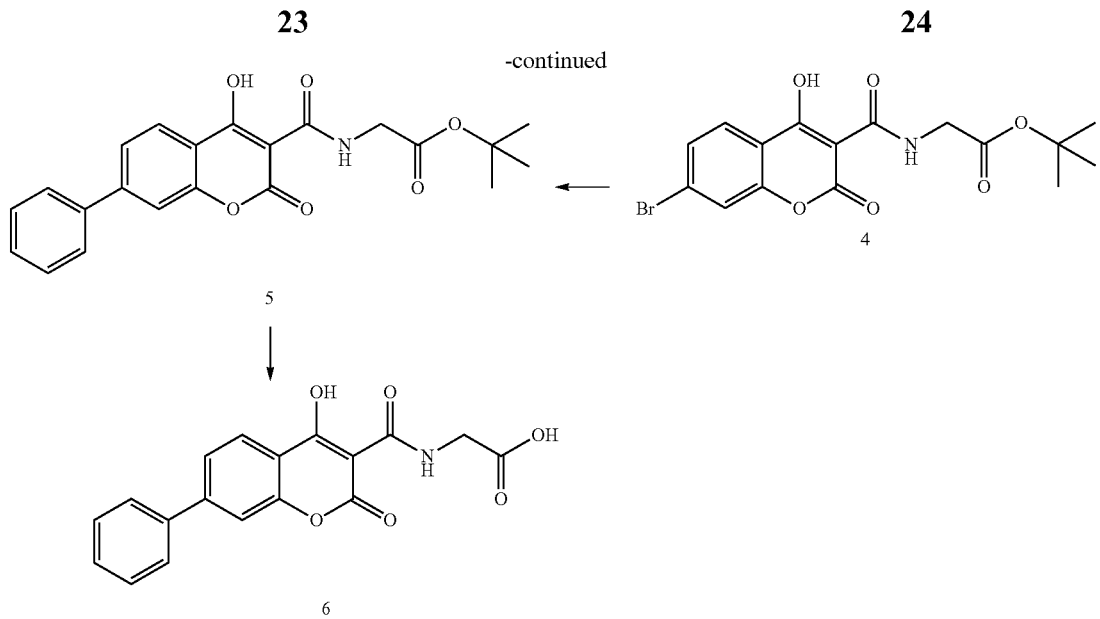

Reagent 1 (42 g, 33.6 mmol) was dissolved in 200 mL of AC$_2$O with addition of 1 mL of H$_3$PO$_4$, and was heated at 50° C. After its completion, the reaction mixture was cooled to room temperature, and 500 mL of water was then added in and stirred at 50° C. until hydrolyzation is complete. The reaction mixture was then cooled to 0° C. and filtered. The resulting solid, Compound 2, was further dried (47 g).

Compound 2 (25.9 g, 100 mmol) and 1-Hydroxybenzotriazole anhydrous (HOBt, 13.5 g) was dissolved in 400 mL of THF. Dicyclohexylcarbodiimide (DCC, 20.9 g) was gradually added in at 0° C. and stirred over night at a temperature below 10° C. The reaction mixture was filtered and the Filtrate A was collected. 13.2 g (100 mmol) of dimethyl malonate was dissolved in 800 mL of THF first, then 7.2 g sodium hydride (70% dispersion) was added in. Filtrate A was added while stirred and left to react for 2 hours at room temperature. After THF removed by vacuum distillation, 400 mL of methanol and 400 mL of 10% HCl were added and stirred over night. After filtration, the resulting solid was washed with 400 mL of methanol and dried, yielding 14 g of Compound 3.

Glycine t-butyl ester HCl salt (13.4 g) and sodium methoxide (4.4 g) were suspended in 200 mL of methanol. After stirred to a homogeneous suspension, it was distilled to remove all methanol. 200 mL of THF and Compound 3 (6.0 g) were added in and the reaction was run at 60° C. over night. THF was then removed by vacuum distillation and 400 mL of methanol was added and stirred for 2 hours. After filtration and drying, it gave 4.5 g of Compound 4.

Compound 4 (240 mg, 0.6 mmol), Pd(PPh$_3$)$_4$ (140 mg, 0.12 mmol) and phenyl boronic acid (85.4 mg, 0.7 mmol) were dissolved in 1 mL of 2M Na$_2$CO$_3$ aqueous solution and 4 mL of DMF. The resulting solution was heated to 80° C. under nitrogen gas overnight. After its completion, the reaction mixture was cooled to room temperature. 100 L of water and 100 mL of ethyl acetate were added and stirred. The organic layer was retained and washed twice more by water, followed by quickly passing through a silicon gel column to remove solvent. 5 mL of dichloromethane and 5 mL of trifluoroacetic acid were then added and stirred at room temperature for 4 hrs. After its completion, the reaction mixture was evaporated in vacuo. The resulting product was further purified by recrystallization using CH$_3$OH-THF to arrive at the title compound 6, with the LC-MS [M-H]$^-$ m/z 338, and $^1$H-NMR (300 MHz, (CD$_3$)$_2$SO) δ 13.01 (br s, 1H), 9.55 (br s, 1H), 8.05 (d, 1H, J=9.0 Hz), 7.85 (d, 1H, J=9.0 Hz), 7.83 (t, 1H, J=7.5 Hz), 7.82 (dd, 2H, J=7.5, 7.5 Hz), 7.54 (dd, 2H, J=7.5, 1.5 Hz), 7.46 (s, 1H), 4.14 (d, 2H, J=6.0 Hz).

Example 2

Synthesis of N-[(4-hydroxy-2-oxo-7-(2-chloro-phenyl)-2H-3-chromenyl)carbonyl]glycine

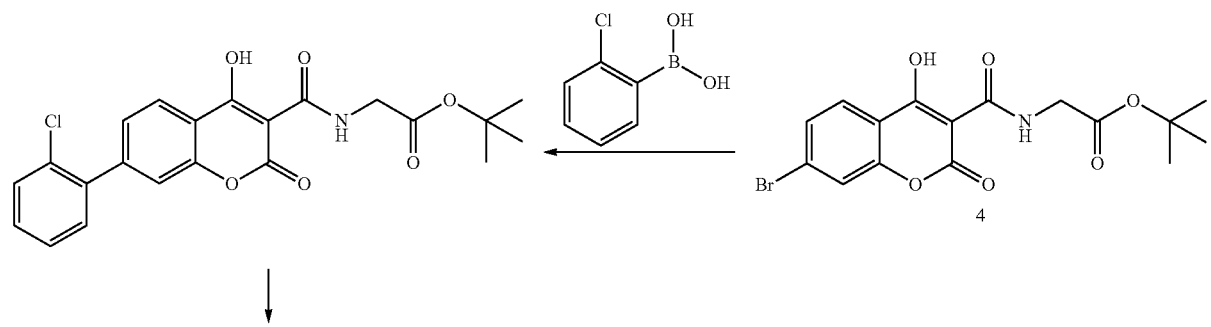

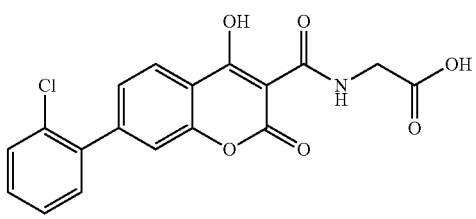

Similar procedure to the previous example was followed to arrive at the title compound, with the LC-MS [M-H]⁻ m/z 373, and ¹H-NMR (300 MHz, (CD$_3$)$_2$SO) δ 13.05 (br s, 1H), 9.57 (br s, 1H), 8.08 (d, 1H, J=8.4 Hz), 7.66-7.32 (m, 6H), 4.15 (d, 2H, J=6.0 Hz).

Example 3

Synthesis of N-[(4-hydroxy-2-oxo-7-(3-chloro-phenyl)-2H-3-chromenyl)carbonyl]glycine

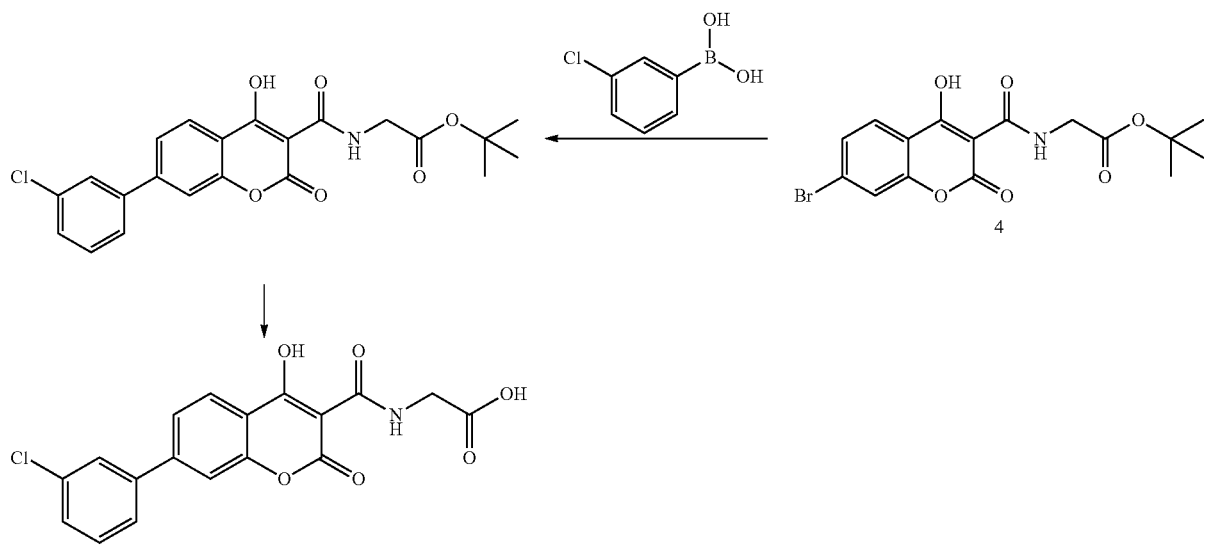

Similar procedure to the previous example was followed to arrive at the title compound, with the LC-MS [M-H]⁻ m/z 373, and ¹H-NMR (300 MHz, (CD$_3$)$_2$SO) δ 13.05 (br s, 1H), 9.55 (br s, 1H), 8.04 (d, 1H, J=8.4 Hz), 7.92-7.81 (m, 4H), 7.59-7.55 (m, 2H), 4.14 (d, 2H, J=6.0 Hz).

Example 4

Synthesis of N-[(4-hydroxy-2-oxo-7-(4-chloro-phenyl)-2H-3-chromenyl)carbonyl]glycine

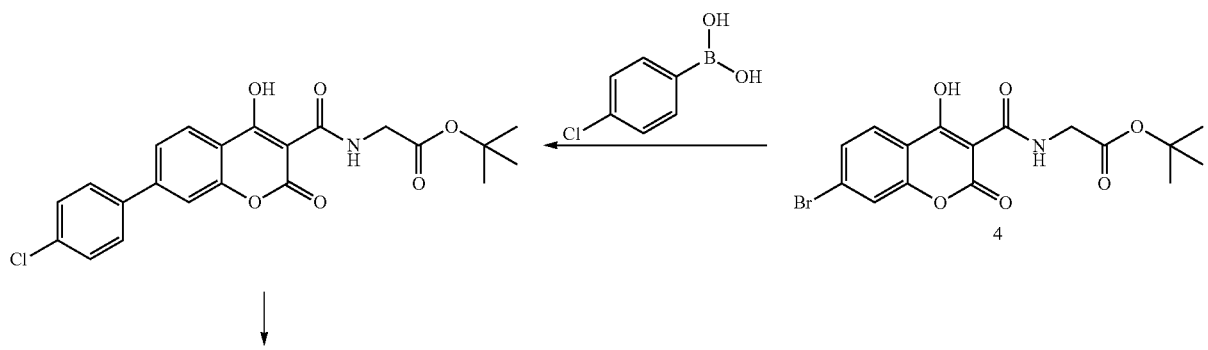

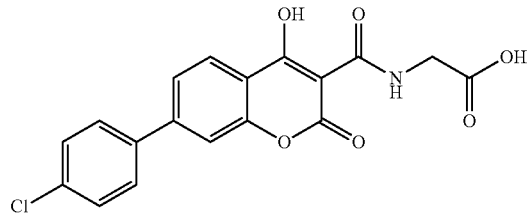

Similar procedure to the previous example was followed to arrive at the title compound, with the LC-MS [M-H]⁻ m/z 373, and ¹H-NMR (300 MHz, (CD$_3$)$_2$SO) δ 9.55 (br s, 1H), 8.05 (d, 1H, J=8.4 Hz), 7.88 (d, 2H, J=8.7 Hz), 7.84-7.79 (m, 2H), 7.60 (d, 2H, J=8.7 Hz), 4.14 (d, 2H, J=6.0 Hz).

Example 5

Synthesis of N-[(4-hydroxy-2-oxo-7-(3-trifluoromethyl-phenyl)-2H-3-chromenyl)carbonyl]glycine

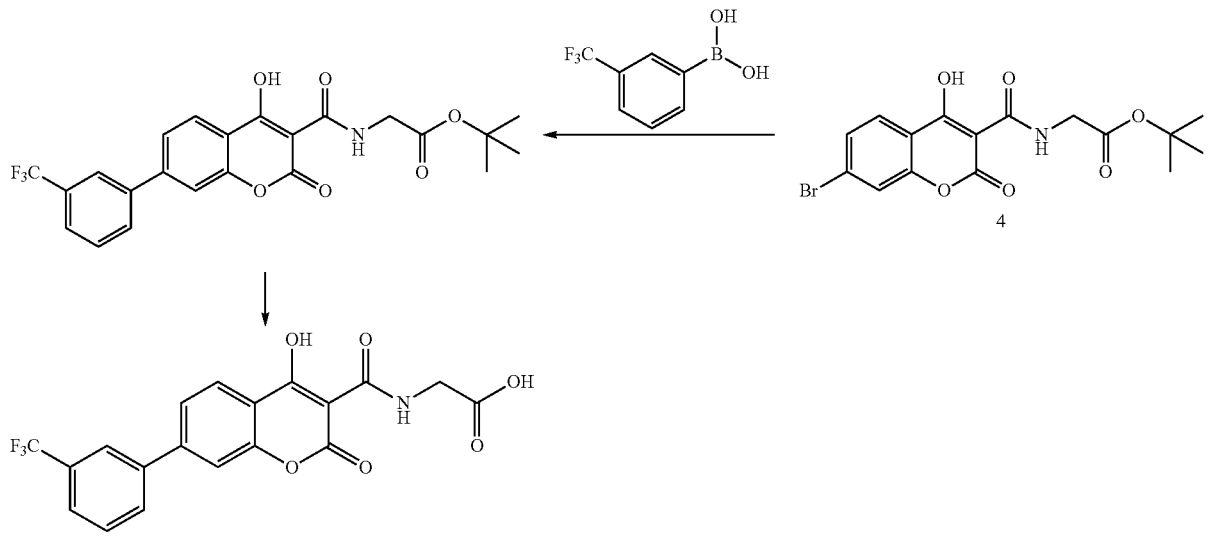

Similar procedure to the previous example was followed to arrive at the title compound, with the LC-MS [M-H]⁻ m/z 406, and ¹H-NMR (300 MHz, (CD$_3$)$_2$SO) δ 9.58 (br s, 1H), 8.18 (s, 1H), 8.16 (s, 1H), 8.09 (d, 1H, J=8.4 Hz), 7.97-7.76 (m, 4H), 4.15 (d, 2H, J=6.0 Hz).

Example 6

Synthesis of N-[(4-hydroxy-2-oxo-7-(4-trifluoromethyl-phenyl)-2H-3-chromenyl)carbonyl]glycine

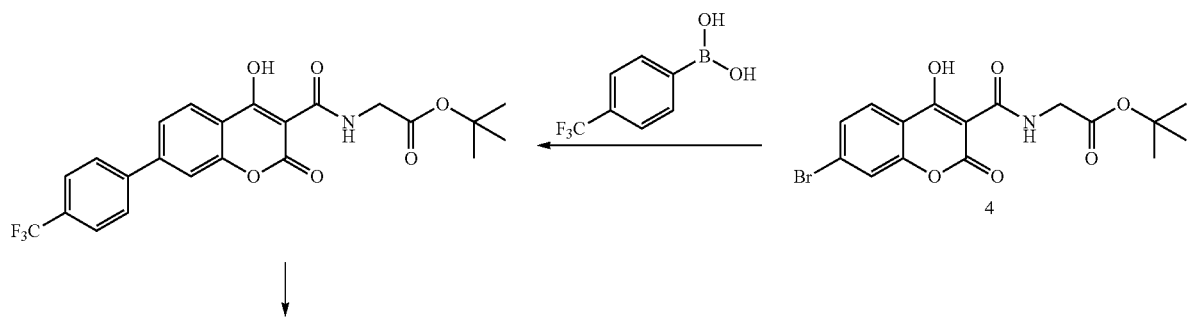

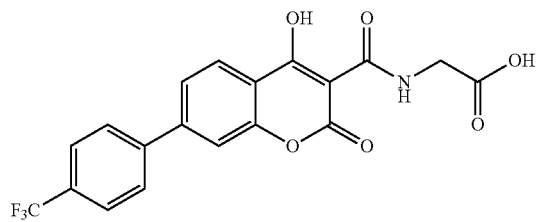

Similar procedure to the previous example was followed to arrive at the title compound, with the LC-MS [M-H]⁻ m/z 406, and ¹H-NMR (300 MHz, $(CD_3)_2SO$) δ 9.56 (br s, 1H), 8.11-8.05 (m, 3H), 7.91-7.84 (m, 4H), 4.15 (d, 2H, J=6.0 Hz).

Example 7

Synthesis of N-[(4-hydroxy-2-oxo-7-(3-trifluoromethoxy-phenyl)-2H-3-chromenyl)carbonyl]glycine

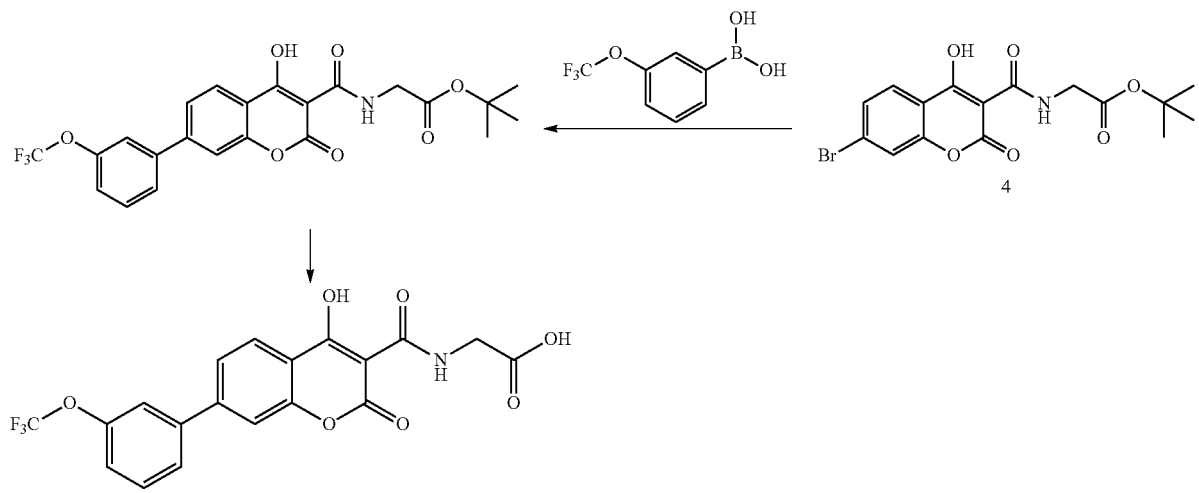

Similar procedure to the previous example was followed to arrive at the title compound, with the LC-MS [M-H]⁻ m/z 422, and ¹H-NMR (300 MHz, $(CD_3)_2SO$) δ 9.57 (br s, 1H), 8.08 (d, 1H, J=8.1 Hz), 7.92-7.85 (m, 4H), 7.69 (t, 1H), 7.50 (d, 1H, J=8.4 Hz), 4.15 (d, 2H, J=6.0 Hz).

Example 8

Synthesis of N-[(4-hydroxy-2-oxo-7-(4-trifluoromethoxy-phenyl)-2H-3-chromenyl)carbonyl]glycine

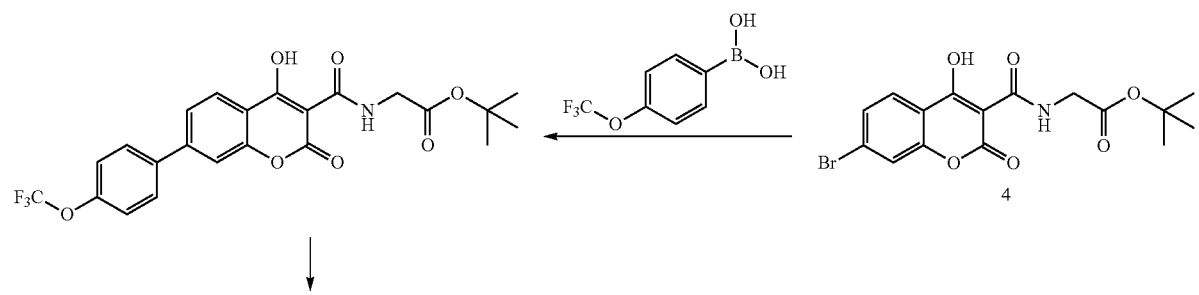

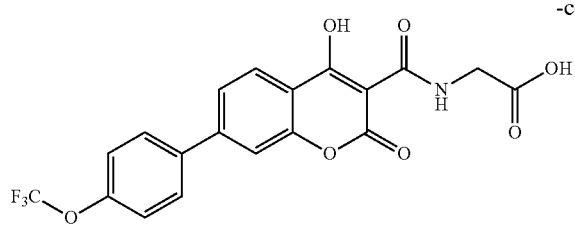

Similar procedure to the previous example was followed to arrive at the title compound, with the LC-MS [M-H]⁻ m/z 422, and ¹H-NMR (300 MHz, (CD$_3$)$_2$SO) δ 9.56 (br s, 1H), 8.09-7.81 (m, 5H), 7.54 (d, 2H, J=8.4 Hz), 4.15 (d, 2H, J=6.0 Hz).

Example 9

Synthesis of N-[(4-hydroxy-2-oxo-7-(3,4-dichlorophenyl)-2H-3-chromenyl)carbonyl]glycine

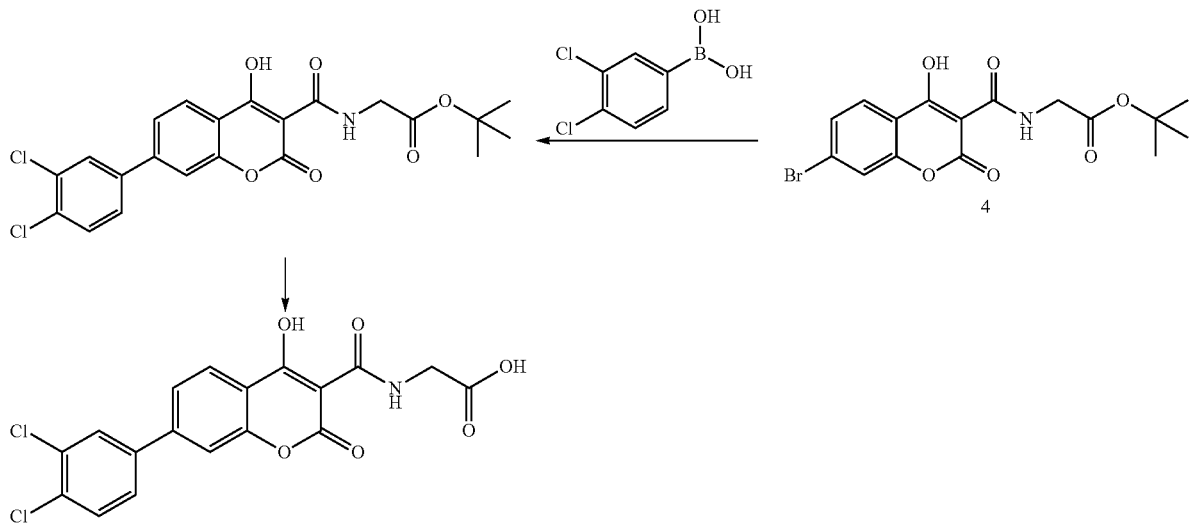

Similar procedure to the previous example was followed to arrive at the title compound, with the LC-MS [M-H]⁻ m/z 407, and ¹H-NMR (300 MHz, (CD$_3$)$_2$SO) δ 9.57 (br s, 1H), 8.15 (s, 1H), 8.05 (d, 1H, J=8.1 Hz), 7.92-7.78 (m, 4H), 4.15 (d, 2H, J=6.0 Hz).

Example 10

Synthesis of N-[(4-hydroxy-2-oxo-7-(3,4-difluorophenyl)-2H-3-chromenyl)carbonyl]glycine

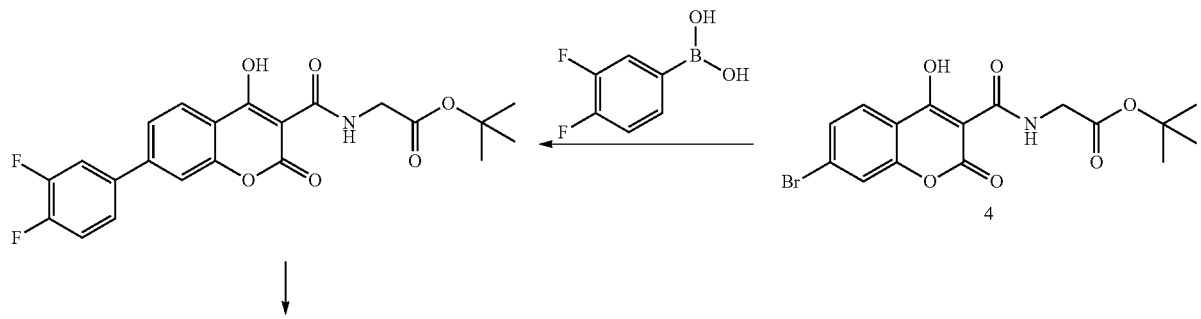

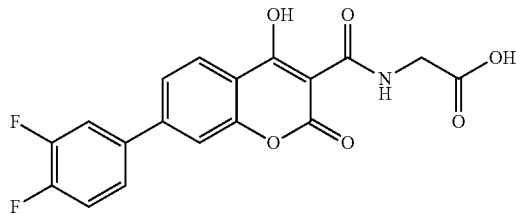

Similar procedure to the previous example was followed to arrive at the title compound, with the LC-MS [M-H]⁻ m/z 374, and ¹H-NMR (300 MHz, (CD$_3$)$_2$SO) δ 9.55 (br s, 1H), 8.07-7.98 (m, 2H), 7.88-7.82 (m, 2H), 7.66-7.59 (m, 2H), 4.14 (d, 2H, J=6.0 Hz).

Example 11
Synthesis of N-[(4-hydroxy-2-oxo-7-(3,4,5-trifluorophenyl)-2H-3-chromenyl)carbonyl]glycine

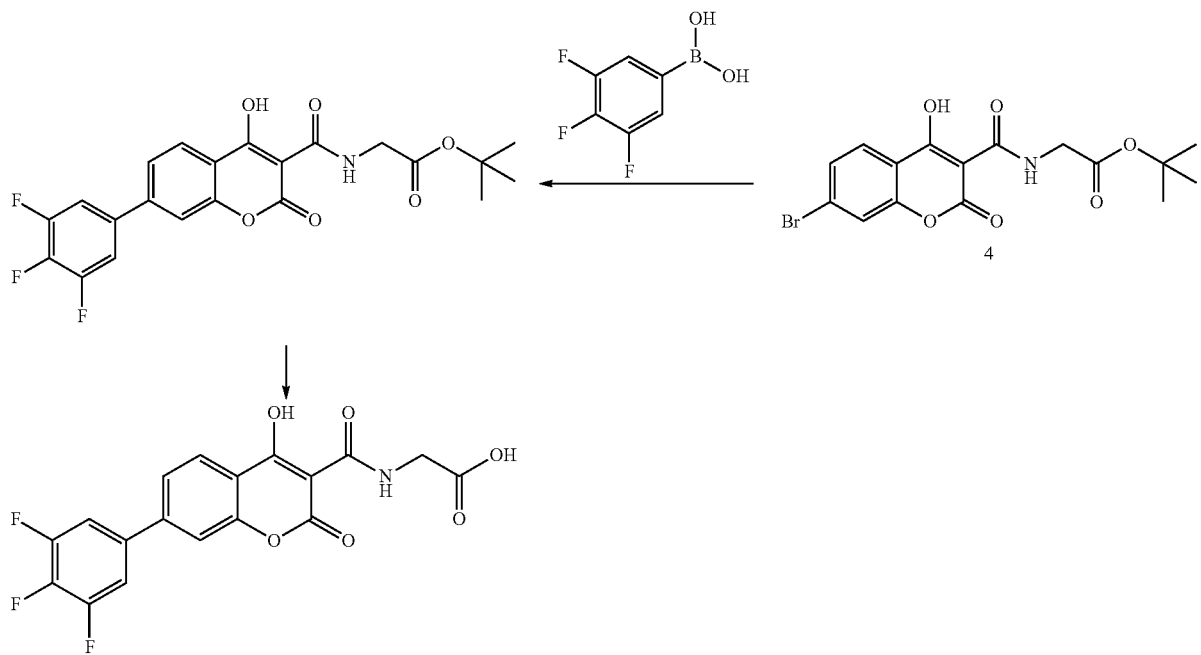

Similar procedure to the previous example was followed to arrive at the title compound, with the LC-MS [M-H]⁻ m/z 392, and ¹H-NMR (300 MHz, (CD$_3$)$_2$SO) δ 9.55 (br s, 1H), 8.05 (d, 1H, J=8.4 Hz), 7.97-7.85 (m, 4H), 4.14 (d, 2H, J=6.0 Hz).

Example 12
Synthesis of N-[(4-hydroxy-2-oxo-7-(3-methoxyphenyl)-2H-3-chromenyl)carbonyl]glycine

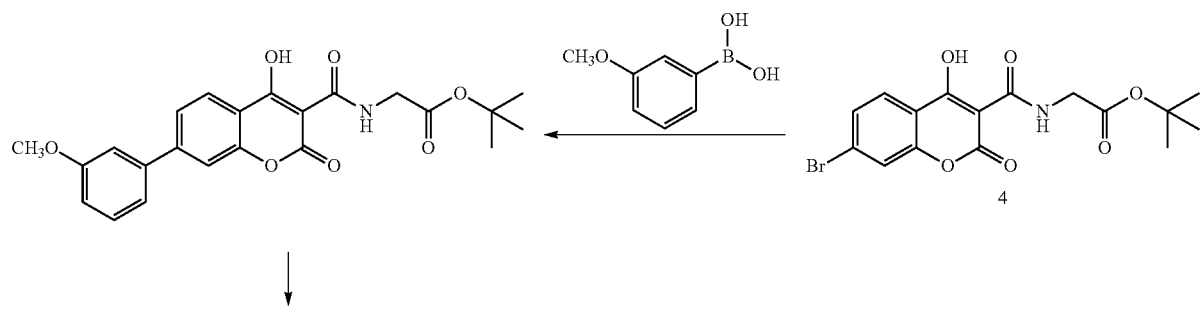

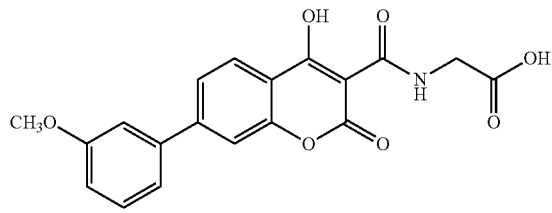

Similar procedure to the previous example was followed to arrive at the title compound, with the LC-MS [M-H]⁻ m/z 368, and $^1$H-NMR (300 MHz, (CD$_3$)$_2$SO) δ 9.55 (br s, 1H), 8.05 (d, 1H, J=8.1 Hz), 7.86 (s, 1H), 7.83 (d, 1H, J=8.1 Hz), 7.49-7.38 (m, 3H), 7.06 (d, 1H, J=8.4 Hz), 4.15 (d, 2H, J=6.0 Hz).

Example 13

Synthesis of N-[(4-hydroxy-2-oxo-7-(4-methoxyphenyl)-2H-3-chromenyl)carbonyl]glycine

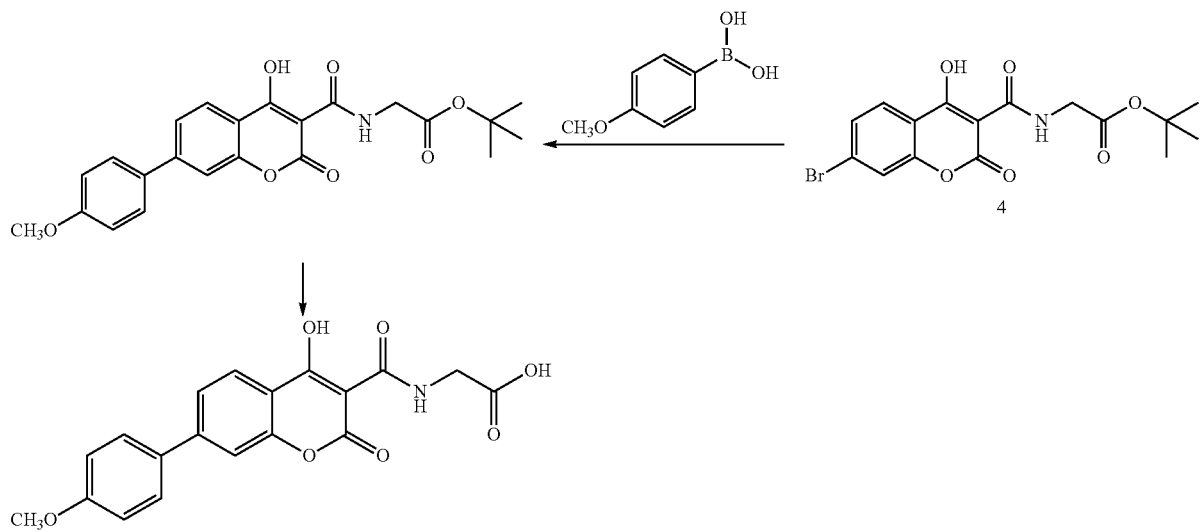

Similar procedure to the previous example was followed to arrive at the title compound, with the LC-MS [M-H]⁻ m/z 368, and $^1$H-NMR (300 MHz, (CD$_3$)$_2$SO) δ 9.56 (br s, 1H), 8.02 (d, 1H, J=8.7 Hz), 7.85-7.78 (m, 4H), 7.09 (d, 2H, J=9.0 Hz), 4.14 (d, 2H, J=6.0 Hz).

Example 14

Synthesis of N-[(4-hydroxy-2-oxo-7-(3-methylphenyl)-2H-3-chromenyl)carbonyl]glycine

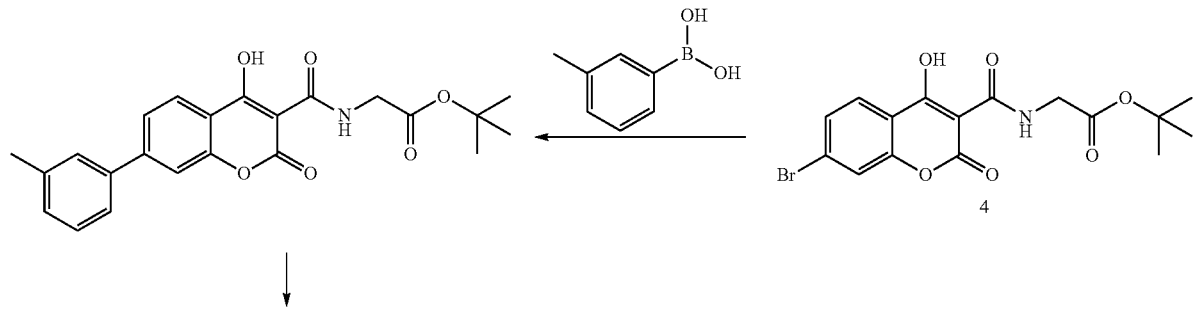

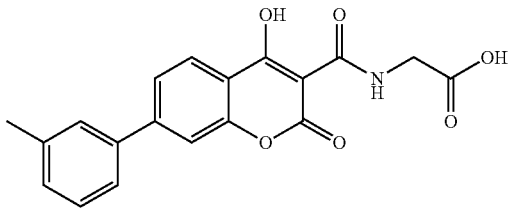

10

Similar procedure to the previous example was followed to arrive at the title compound, with the LC-MS [M-H]⁻ m/z 352, and ¹H-NMR (300 MHz, (CD$_3$)$_2$SO) δ 9.55 (br s, 1H), 8.04 (d, 1H, J=8.7 Hz), 7.80-7.78 (m, 2H), 7.67-7.61 (m, 2H), 7.42 (t, 1H, 7.8 Hz), 7.30 (d, 1H, J=7.5 Hz), 4.14 (d, 2H, J=6.0 Hz), 2.50 (t, 3H, 1.8 Hz).

Example 15
Synthesis of N-[(4-hydroxy-2-oxo-7-(4-methylphenyl)-2H-3-chromenyl)carbonyl]glycine

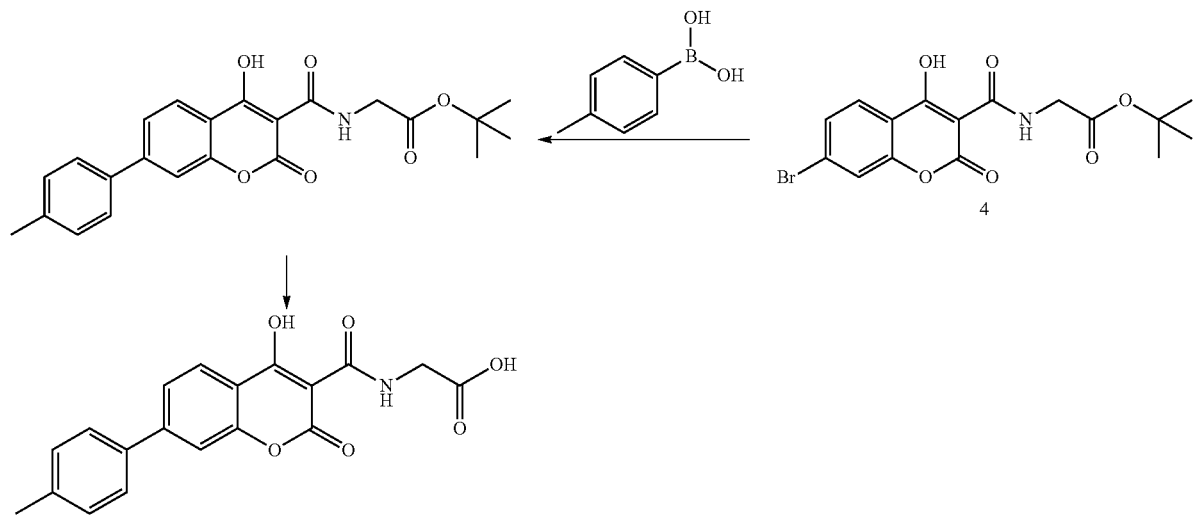

Similar procedure to the previous example was followed to arrive at the title compound, with the LC-MS [M-H]⁻ m/z 352, and ¹H-NMR (300 MHz, (CD$_3$)$_2$SO) δ 9.56 (br s, 1H), 8.02 (d, 1H, J=8.7 Hz), 7.79-7.73 (m, 4H), 7.34 (d, 2H, J=8.4 Hz), 4.13 (d, 2H, J=6.0 Hz), 2.50 (t, 3H, 1.8 Hz).

Example 16
Synthesis of N-[(4-hydroxy-2-oxo-8-phenyl-2H-3-chromenyl)carbonyl]glycine

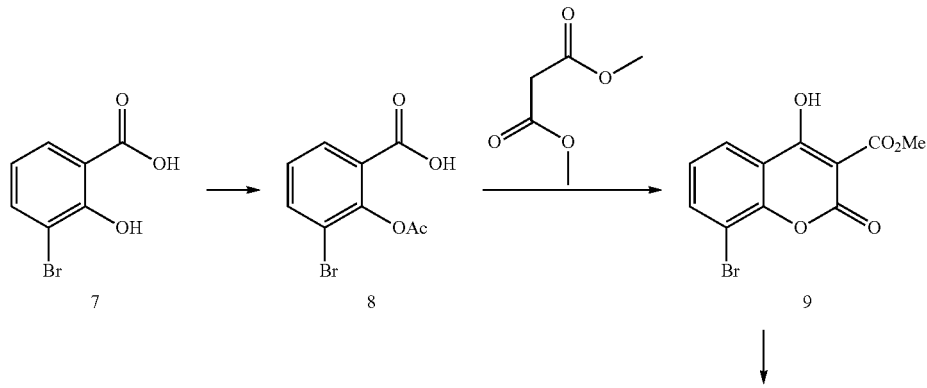

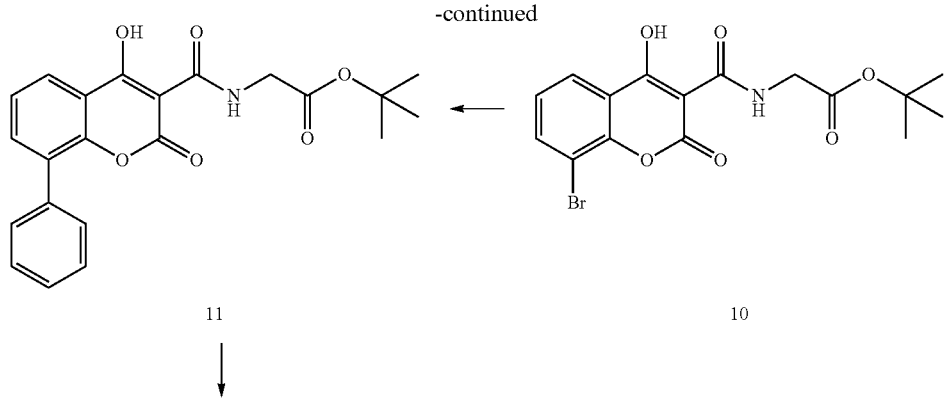

11  ←  10

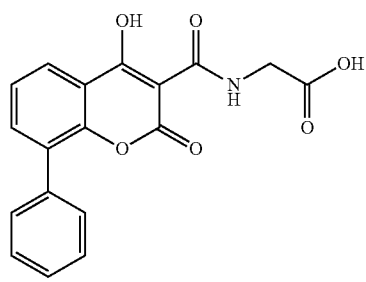

12

Similar to the synthetic procedure of Example 1, Reagent 7 (27 g) was dissolved in 130 mL of $Ac_2O$ with addition of 1 mL of $H_3PO_4$, and was heated at 50° C. After its completion, the reaction mixture was cooled to room temperature, and 500 mL of water was then added in and stirred at 50° C. until hydrolyzation is complete. The reaction mixture was then cooled to 0° C. and filtered. The resulting solid, Compound 8, was further dried (24.4 g).

Compound 8 (13 g) and 1-Hydroxybenzotriazole anhydrous (HOBt, 6.8 g) was dissolved in 200 mL of THF. Dicyclohexylcarbodiimide (DCC, 10.4 g) was gradually added in at 0° C. and stirred over night at a temperature below 10° C. The reaction mixture was filtered and the Filtrate B was collected. 6.6 g (50 mmol) of dimethyl malonate was dissolved in 400 mL of THF first, then 3.8 g sodium hydride (70% dispersion) was added in. Filtrate B was added while stirred and left to react for 2 hours at room temperature. After THF removed by vacuum distillation, 200 mL of methanol and 200 mL of 10% HCl were added and stirred over night. After filtration, the resulting solid was washed with 200 mL of methanol and dried, yielding 6 g of Compound 9.

Glycine t-butyl ester HCl salt (13.5 g) and sodium methoxide (4.4 g) were suspended in 200 mL of methanol. After stirred to a homogeneous suspension, it was distilled to remove all methanol. 200 mL of THF and Compound 9 (6.0 g) were added in and the reaction was run at 60° C. over night. THF was then removed by vacuum distillation and 400 mL of methanol was added and stirred for 2 hours. After filtration and drying, it gave 3.5 g of Compound 10.

Compound 10 (240 mg, 0.6 mmol), $Pd(PPh_3)_4$ (140 mg, 0.12 mmol) and phenyl boronic acid (85.4 mg, 0.7 mmol) were dissolved in 1 mL of 2M $Na_2CO_3$ aqueous solution and 4 mL of DMF. The resulting solution was heated to 80° C. under nitrogen gas overnight. After its completion, the reaction mixture was cooled to room temperature. 100 mL of water and 100 mL of ethyl acetate were added and stirred. The organic layer was retained and washed twice more by water, followed by quickly passing through a silicon gel column to remove solvent. 5 mL of dichloromethane and 5 mL of trifluoroacetic acid were then added and stirred at room temperature for 4 hrs. After its completion, the reaction mixture was evaporated in vacuo. The resulting product was further purified by recrystallization using $CH_3OH$-THF to arrive at the title compound 12, with the LC-MS [M-H]$^-$ m/z 338, and $^1$H-NMR (300 MHz, $(CD_3)_2SO$) δ 9.51 (br s, 1H), 8.03 (dd, 1H, J=8.1, 1.5 Hz), 7.86 (dd, 2H, J=7.5, 1.5 Hz), 7.65-7.45 (m, 6H), 4.15 (d, 2H, J=6.0 Hz).

Example 17
Synthesis of N-[(4-hydroxy-2-oxo-8-(2-chlorophenyl)-2H-3-chromenyl)carbonyl]glycine
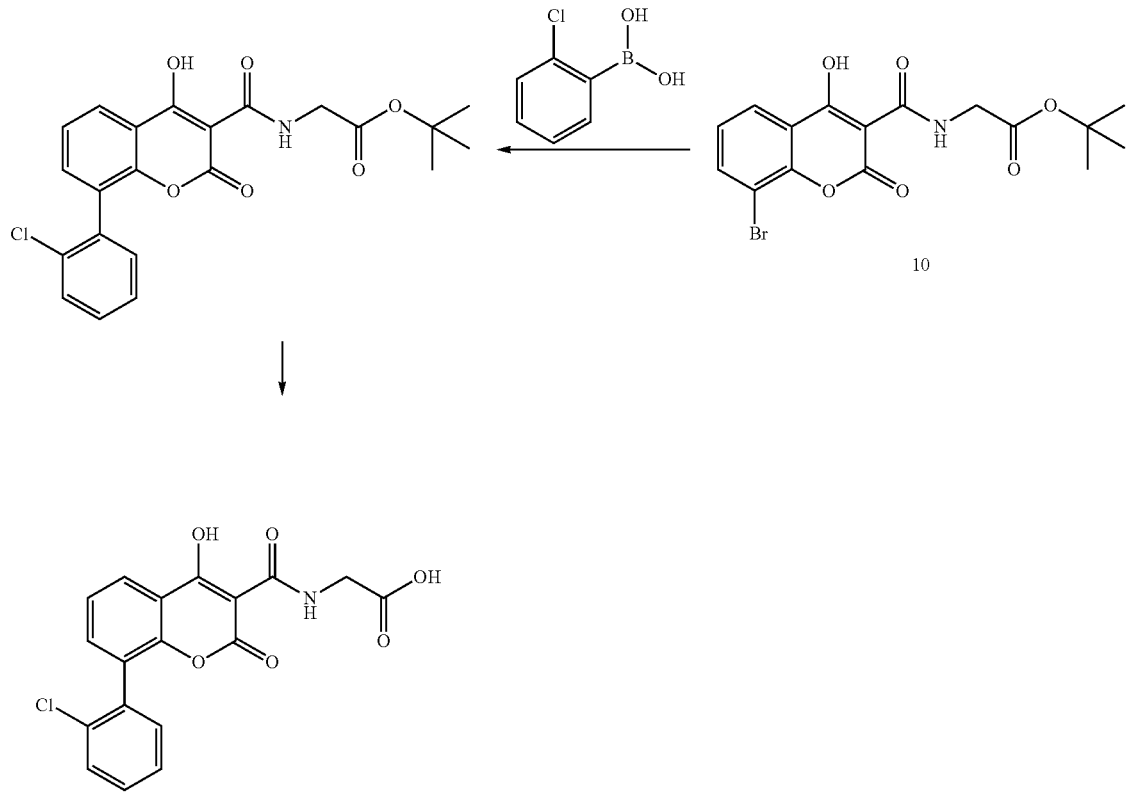
Similar procedure to the previous example was followed to arrive at the title compound, with the LC-MS [M-H]⁻ m/z 373, and ¹H-NMR (300 MHz, (CD$_3$)$_2$SO) δ 9.47 (br s, 1H), 8.10 (m, 1H), 7.77 (m, 1H), 7.67-7.50 (m, 5H), 4.14 (d, 2H, J=6.0 Hz).
Example 18
Synthesis of N-[(4-hydroxy-2-oxo-8-(3-chlorophenyl)-2H-3-chromenyl)carbonyl]glycine
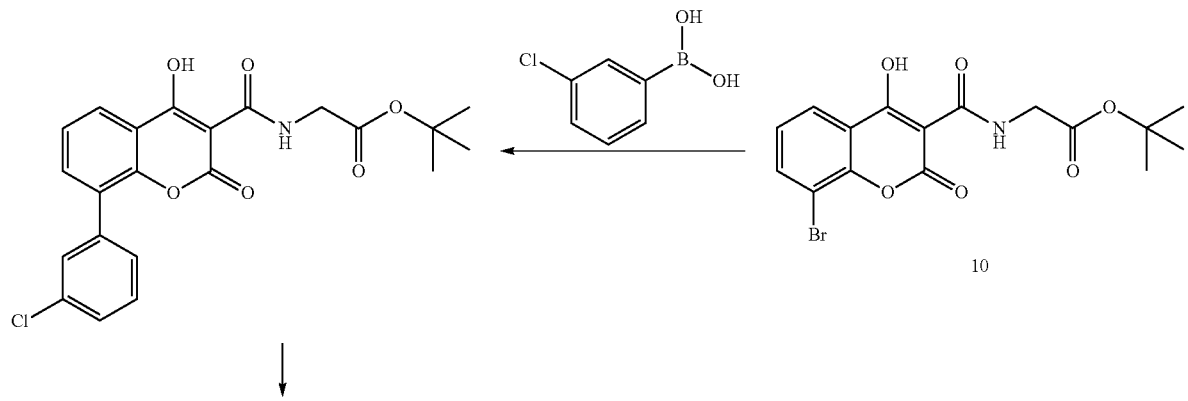

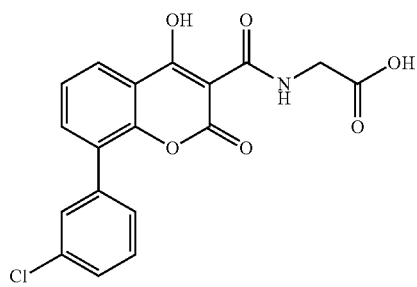

Similar procedure to the previous example was followed to arrive at the title compound, with the LC-MS [M-H]⁻ m/z 373, and ¹H-NMR (300 MHz, (CD$_3$)$_2$SO) δ 9.51 (br s, 1H), 8.06 (dd, 1H, J=8.1, 1.5 Hz), 7.89 (m, 1H), 7.73 (s, 1H), 7.61-7.54 (m, 4H), 4.15 (d, 2H, J=6.0 Hz).

Example 19

Synthesis of N-[(4-hydroxy-2-oxo-8-(4-chlorophenyl)-2H-3-chromenyl)carbonyl]glycine

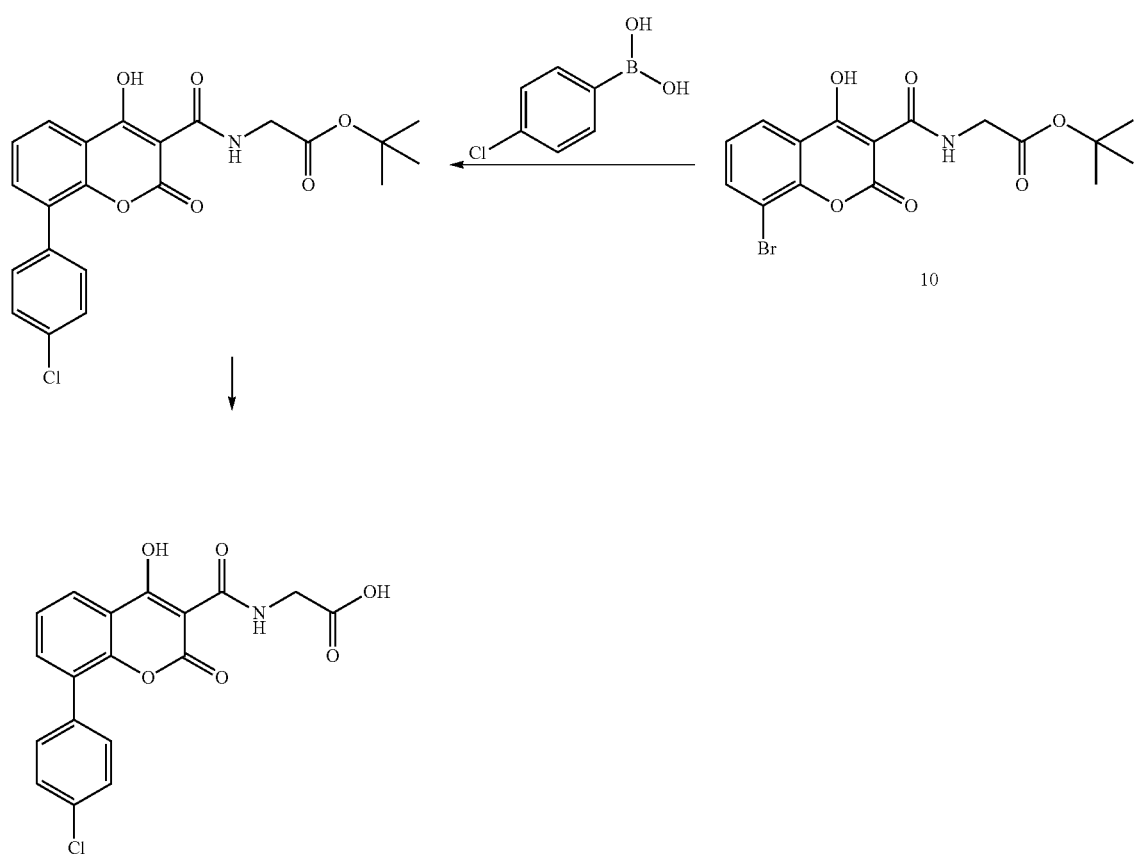

Similar procedure to the previous example was followed to arrive at the title compound, with the LC-MS [M-H]⁻ m/z 373, and ¹H-NMR (300 MHz, (CD$_3$)$_2$SO) δ 9.49 (br s, 1H), 8.04 (dd, 1H, J=8.1, 1.5 Hz), 7.86 (m, 1H), 7.69-7.53 (m, 5H), 4.15 (d, 2H, J=6.0 Hz).

Example 20
Synthesis of N-[(4-hydroxy-2-oxo-8-(3-trifluoromethylphenyl)-2H-3-chromenyl)carbonyl]glycine
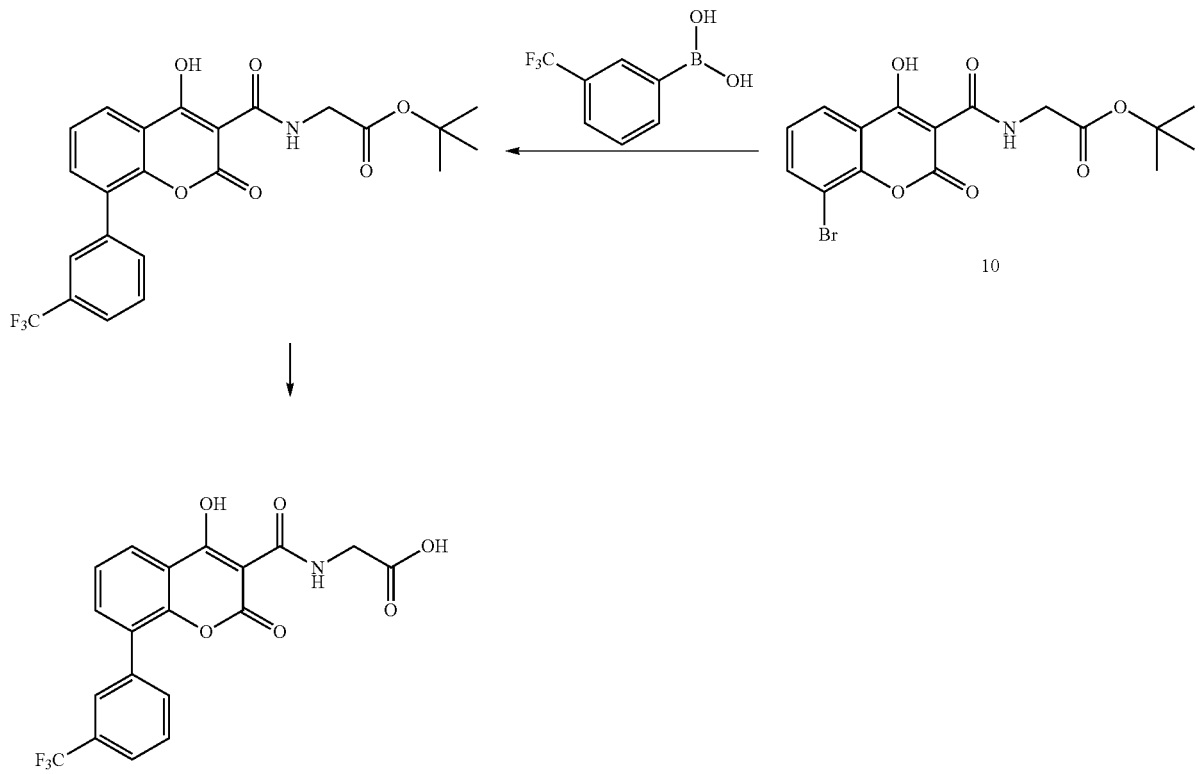
Similar procedure to the previous example was followed to arrive at the title compound, with the LC-MS [M-H]⁻ m/z 406, and ¹H-NMR (300 MHz, (CD$_3$)$_2$SO) δ 9.52 (br s, 1H), 8.09-7.76 (m, 6H), 7.58 (t, 1H, 7.8 Hz), 4.15 (d, 2H, J=6.0 Hz).
Example 21
Synthesis of N-[(4-hydroxy-2-oxo-8-(4-trifluoromethylphenyl)-2H-3-chromenyl)carbonyl]glycine
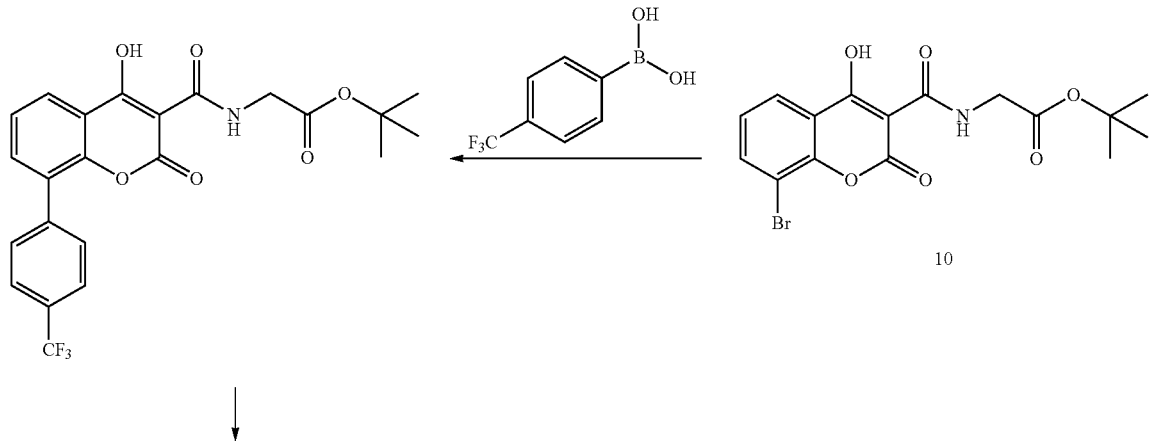

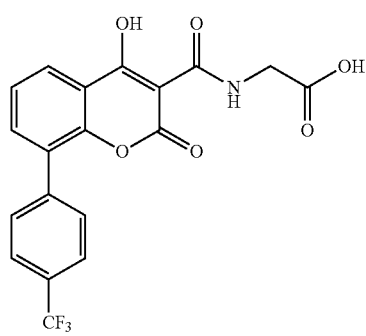

15

Similar procedure to the previous example was followed to arrive at the title compound, with the LC-MS [M-H]⁻ m/z 406, and $^1$H-NMR (300 MHz, (CD$_3$)$_2$SO) δ 9.50 (br s, 1H), 8.09 (dd, 1H, 7.8, 1.5 Hz), 7.93-7.86 (m, 5H), 7.59 (t, 1H, 7.8 Hz), 4.15 (d, 2H, J=6.0 Hz).

Example 22

Synthesis of N-[(4-hydroxy-2-oxo-8-(3-trifluoromethoxyphenyl)-2H-3-chromenyl)carbonyl]glycine

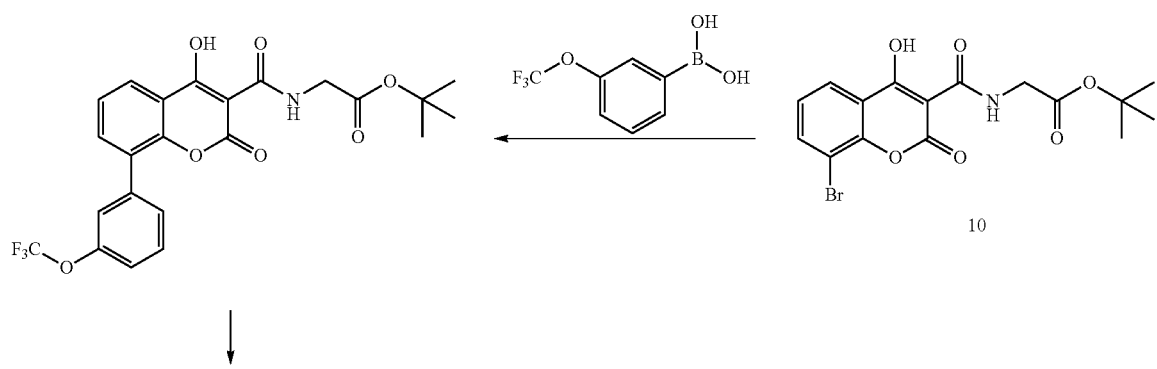

Similar procedure to the previous example was followed to arrive at the title compound, with the LC-MS [M-H]⁻ m/z 422, and $^1$H-NMR (300 MHz, (CD$_3$)$_2$SO) δ 9.52 (br s, 1H), 8.07 (dd, 1H, 7.8, 1.5 Hz), 7.91 (dd, 1H, 7.5, 1.5 Hz), 7.70-7.68 (m, 3H), 7.57 (t, 1H, 7.8 Hz), 7.49 (br s, 1H), 4.15 (d, 2H, J=6.0 Hz).

Example 23
Synthesis of N-[(4-hydroxy-2-oxo-8-(4-trifluoromethoxyphenyl)-2H-3-chromenyl)carbonyl]glycine
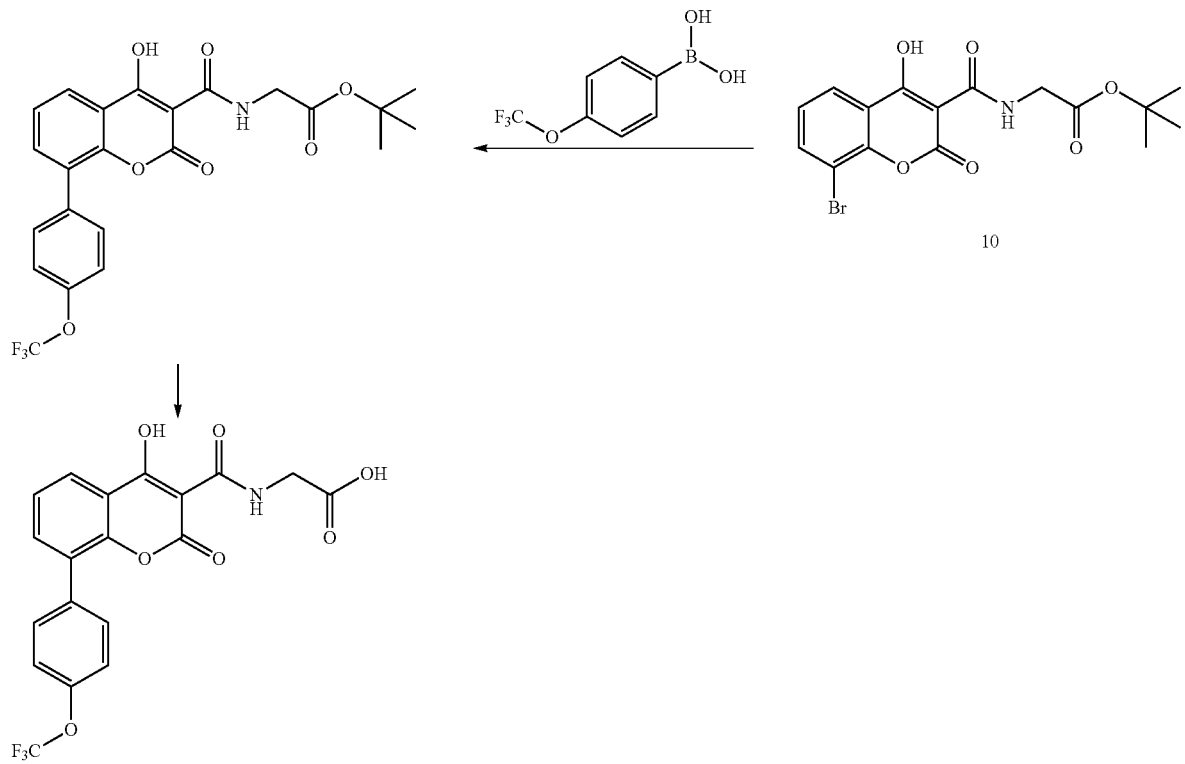
Similar procedure to the previous example was followed to arrive at the title compound, with the LC-MS [M-H]⁻ m/z 422, and ¹H-NMR (300 MHz, (CD$_3$)$_2$SO) δ 9.50 (br s, 1H), 8.06 (dd, 1H, 8.1, 1.5 Hz), 7.89 (m, 1H), 7.78 (d, 2H, J=8.7 Hz), 7.60-7.54 (m, 3H), 4.15 (d, 2H, J=6.0 Hz).
Example 24
Synthesis of N-[(4-hydroxy-2-oxo-8-(3,4-dichlorophenyl)-2H-3-chromenyl)carbonyl]glycine
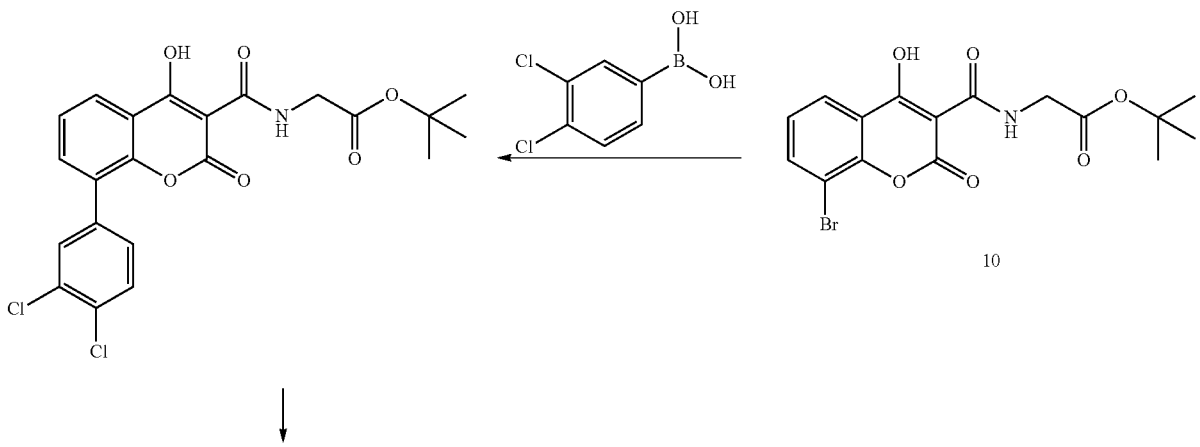

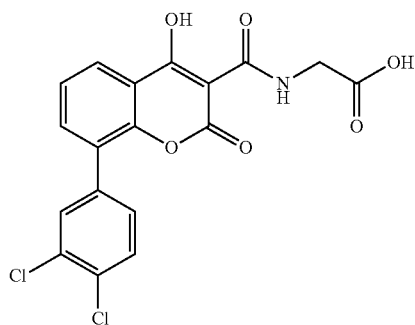

Similar procedure to the previous example was followed to arrive at the title compound, with the LC-MS [M-H]⁻ m/z 407, and ¹H-NMR (300 MHz, (CD$_3$)$_2$SO) δ 9.51 (br s, 1H), 8.06 (dd, 1H, 8.1, 1.5 Hz), 7.95-7.89 (m, 2H), 7.82 (d, 1H, J=8.4 Hz), 7.65 (dd, 1H, J=8.4, 1.5 Hz), 7.56 (t, 1H, J=7.5 Hz), 4.15 (d, 2H, J=6.0 Hz).

Example 25

Synthesis of N-[(4-hydroxy-2-oxo-8-(3,4-difluorophenyl)-2H-3-chromenyl)carbonyl]glycine

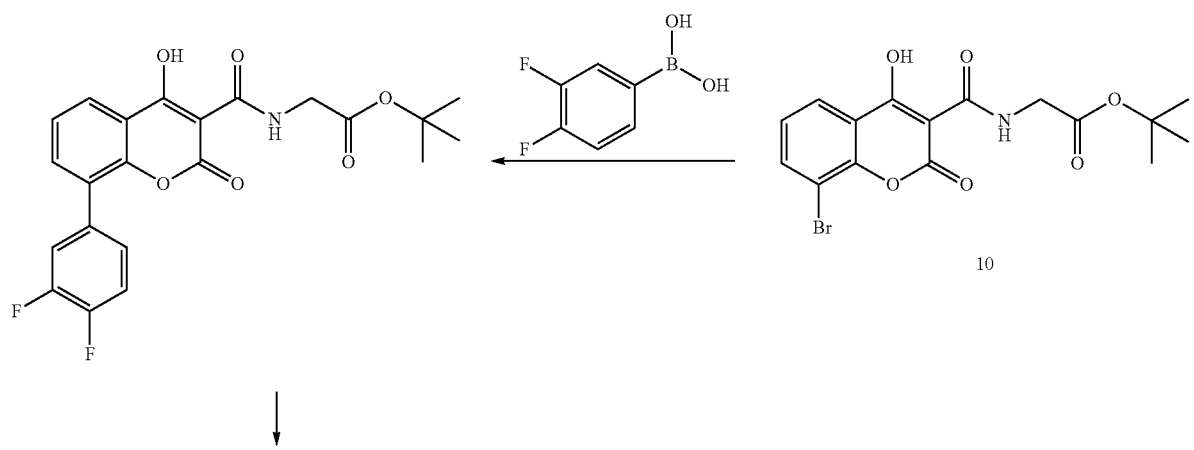

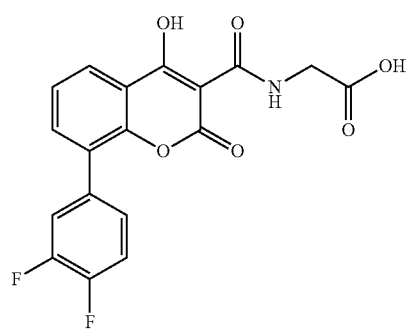

Similar procedure to the previous example was followed to arrive at the title compound, with the LC-MS [M-H]⁻ m/z 374, and ¹H-NMR (300 MHz, (CD$_3$)$_2$SO)O 9.51 (br s, 1H), 7.88 (dd, 1H, J=7.5, 1.2 Hz), 7.82-7.75 (m, 2H), 7.68-7.53 (m, 3H), 4.15 (d, 2H, J=6.0 Hz).

Example 26
Synthesis of N-[(4-hydroxy-2-oxo-8-(3,4,5-trifluorophenyl)-2H-3-chromenyl)carbonyl]glycine
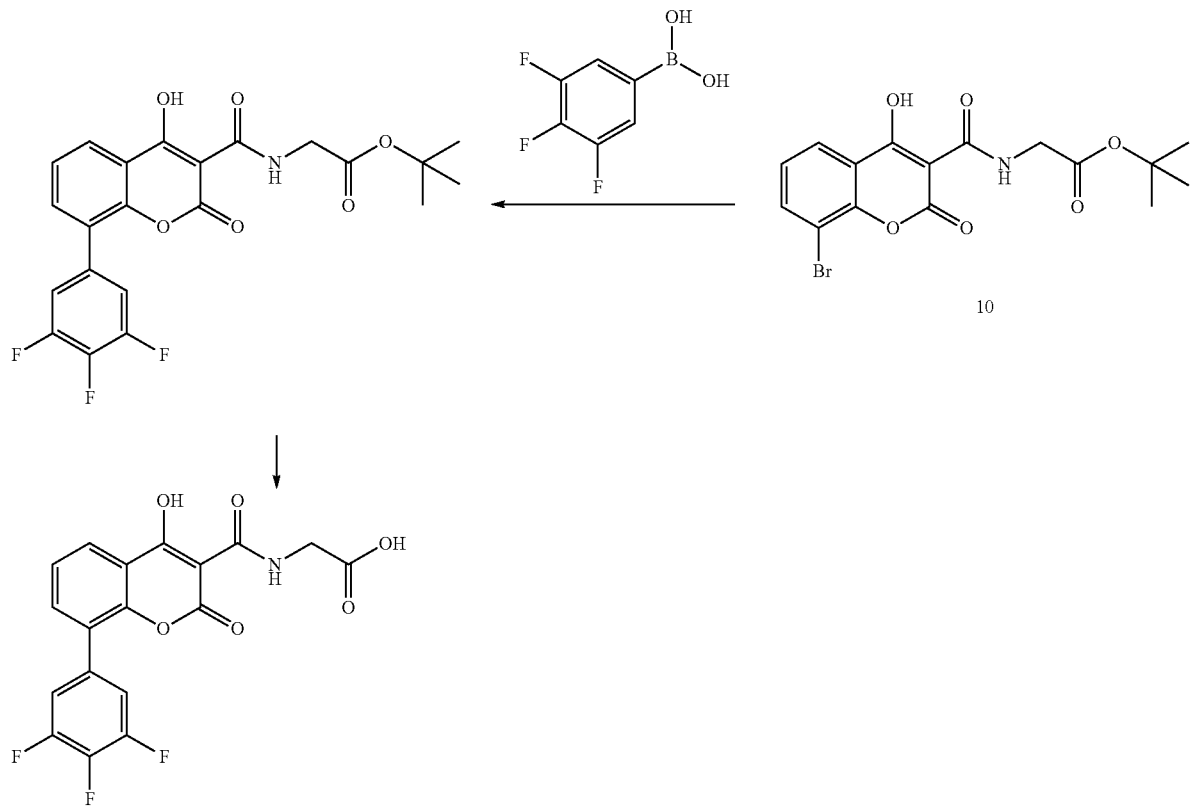
Similar procedure to the previous example was followed to arrive at the title compound, with the LC-MS [M-H]⁻ m/z 392, and ¹H-NMR (300 MHz, (CD$_3$)$_2$SO)O 9.51 (br s, 1H), 8.07 (dd, 1H, J=7.8, 1.5 Hz), 8.01-7.97 (m, 1H), 7.92-7.89 (m, 1H), 7.71-7.66 (m, 1H), 7.63 (t, 1H, J=7.8 Hz), 4.15 (d, 2H, J=6.0 Hz).
Example 27
Synthesis of N-[(4-hydroxy-2-oxo-8-(3-methoxyphenyl)-2H-3-chromenyl)carbonyl]glycine
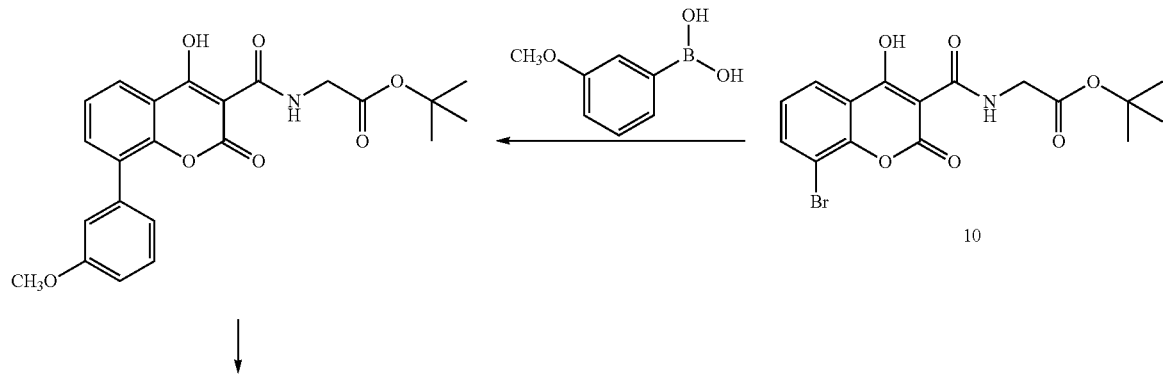

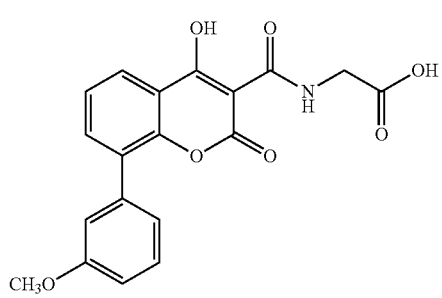

Similar procedure to the previous example was followed to arrive at the title compound, with the LC-MS [M-H]⁻ m/z 368, and ¹H-NMR (300 MHz, (CD$_3$)$_2$SO) δ 9.52 (br s, 1H), 8.07 (dd, 1H, J=7.8, 1.5 Hz), 7.87 (dd, 1H, J=7.8, 1.5 Hz), 7.55 (t, 1H, J=7.8 Hz), 7.45 (t, 1H, J=7.8 Hz), 7.20-7.18 (m, 2H), 7.06-7.03 (m, 1H), 4.15 (d, 2H, J=6.0 Hz).

Example 28

Synthesis of N-[(4-hydroxy-2-oxo-8-(4-methoxyphenyl)-2H-3-chromenyl)carbonyl]glycine

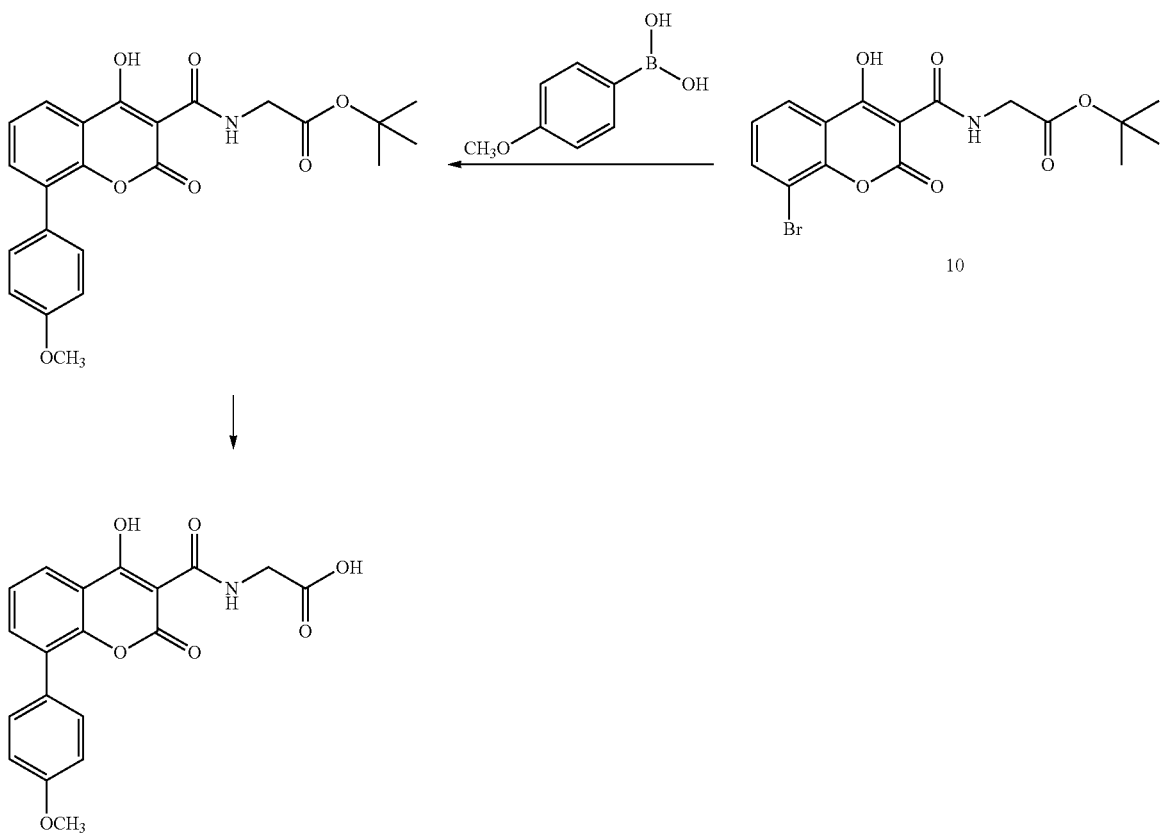

Similar procedure to the previous example was followed to arrive at the title compound, with the LC-MS [M-H]⁻ m/z 368, and ¹H-NMR (300 MHz, (CD$_3$)$_2$SO) δ 9.51 (br s, 1H), 7.98 (d, 1H, J=7.8 Hz), 7.83-7.80 (m, 1H), 7.59-7.50 (m, 3H), 7.09 (d, 2H, J=8.7 Hz), 4.15 (d, 2H, J=6.0 Hz).

Example 29
Synthesis of N-[(4-hydroxy-2-oxo-8-(3-methylphenyl)-2H-3-chromenyl)carbonyl]glycine
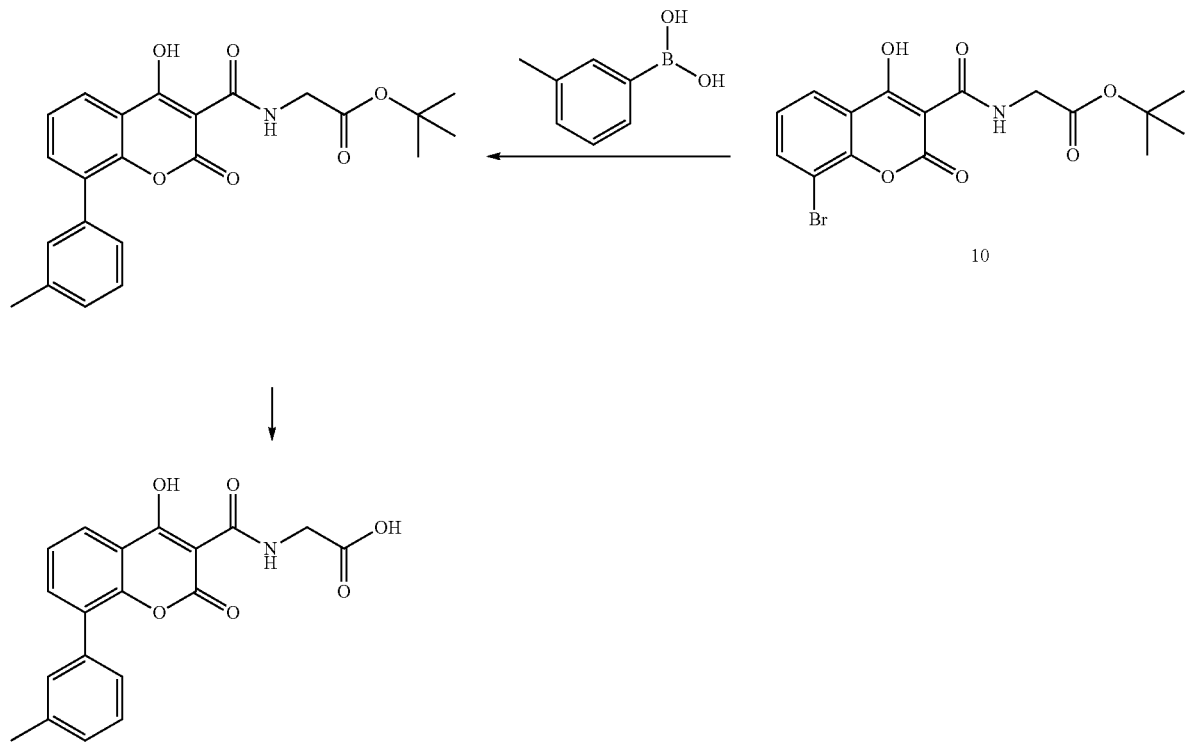
Similar procedure to the previous example was followed to arrive at the title compound, with the LC-MS [M-H]⁻ m/z 352, and $^1$H-NMR (300 MHz, (CD$_3$)$_2$SO)O 9.52 (br s, 1H), 8.03 (dd, 1H, J=7.8, 1.5 Hz), 7.84-7.82 (m, 1H), 7.57-7.52 (m, 1H), 7.43-7.42 (m, 3H), 7.29 (br s, 1H), 4.14 (d, 2H, J=6.0 Hz), 2.51 (t, 3H, J=1.8 Hz).
Example 30
Synthesis of N-[(4-hydroxy-2-oxo-8-(4-methylphenyl)-2H-3-chromenyl)carbonyl]glycine
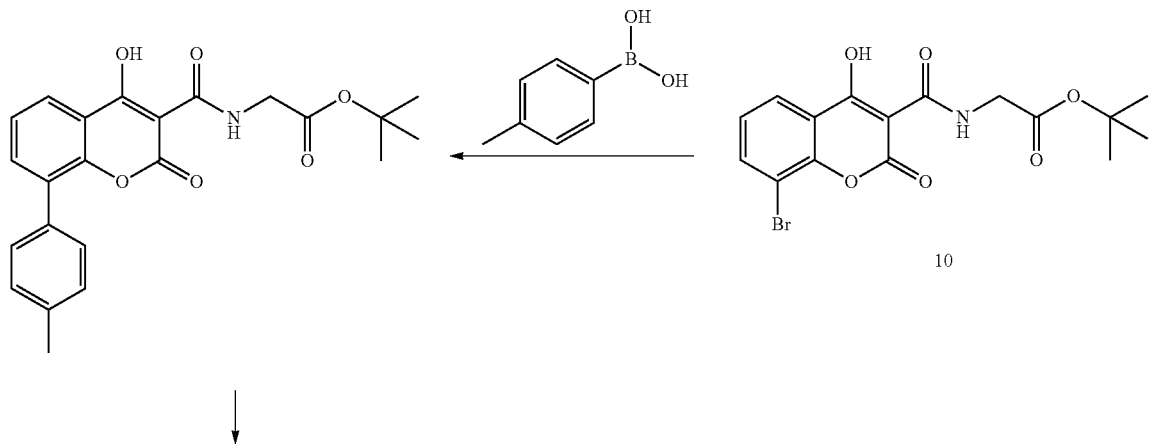

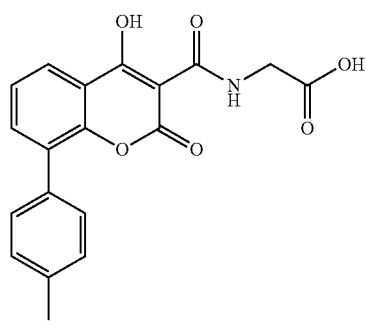

Similar procedure to the previous example was followed to arrive at the title compound, with the LC-MS [M-H]⁻ m/z 352, and ¹H-NMR (300 MHz, (CD$_3$)$_2$SO) δ 9.53 (br s, 1H), 8.02-7.99 (m, 1H), 7.84-7.82 (m, 1H), 7.57-7.51 (m, 3H), 7.36-7.33 (m, 2H), 4.14 (d, 2H, J=6.0 Hz), 2.51 (t, 3H, J=1.8 Hz).

Example 31

Synthesis of N-[(4-hydroxy-2-oxo-7-(6-methoxypyridin-3-yl)-2H-3-chromenyl)carbonyl]glycine

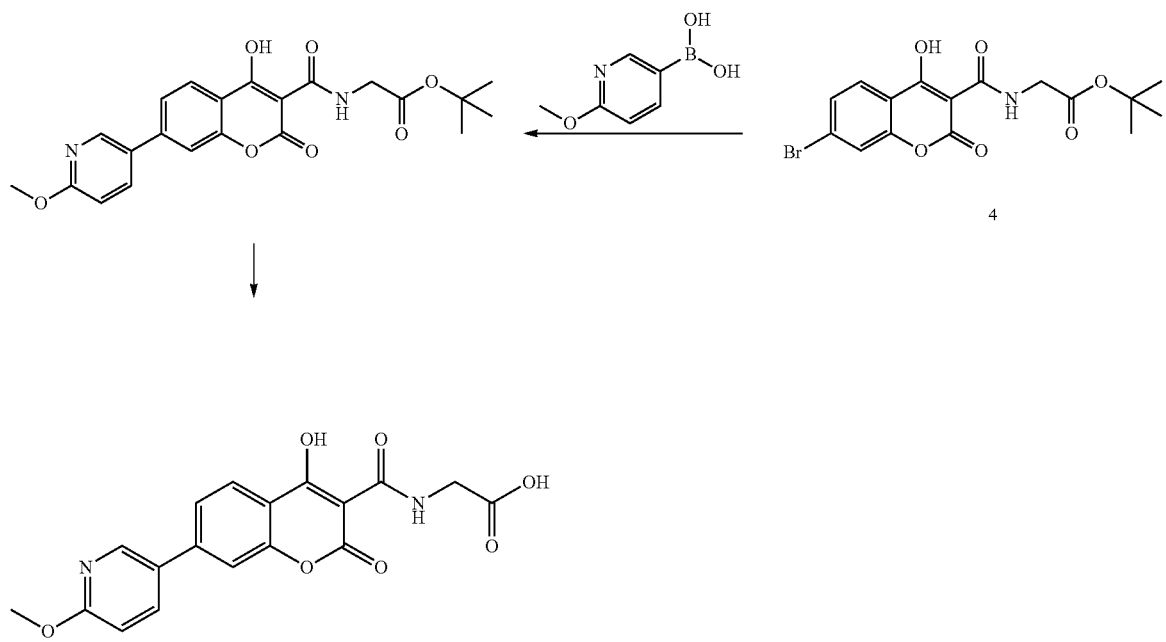

Similar procedure to Example 1 was followed to arrive at the title compound, with the LC-MS [M-H]⁻ m/z 369, and ¹H-NMR (300 MHz, (CD$_3$)$_2$SO) δ 9.54 (br s, 1H), 8.69 (d, 1H, J=1.8 Hz), 8.21 (dd, 1H, J=8.7, 1.8 Hz), 8.023 (d, 1H, 8.1 Hz), 7.85-7.80 (m, 2H), 6.98 (d, 1H, 8.7 Hz), 4.14 (d, 2H, J=6.0 Hz), 2.51 (m, 3H).

Example 32

Synthesis of N-[(4-hydroxy-2-oxo-7-(pyridin-4-yl)-2H-3-chromenyl)carbonyl]glycine

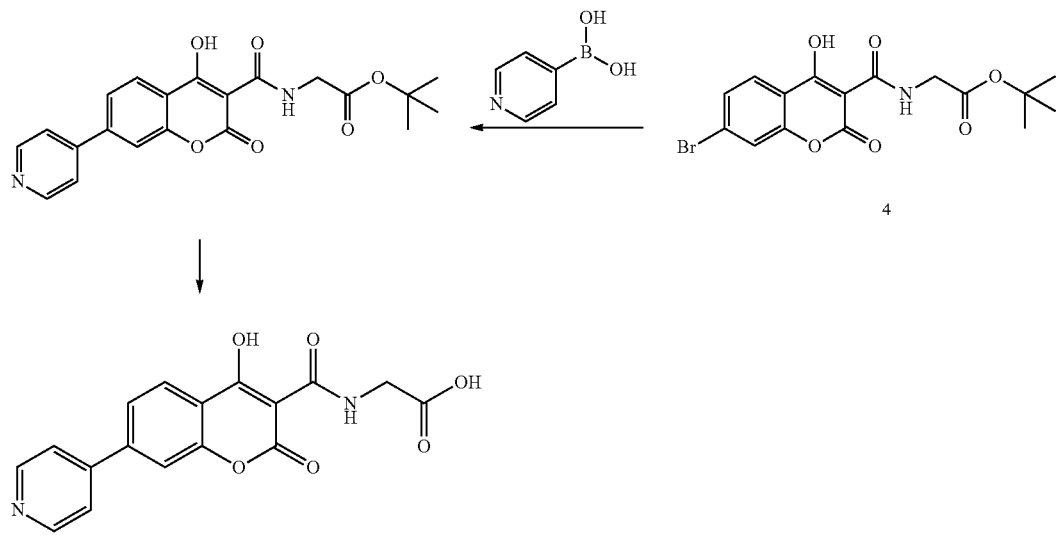 [SMILES: CC(C)(C)OC(=O)CNC(=O)c1c(O)c2ccc(-c3cccnc3)cc2oc1=O ; OB(O)c1cccnc1 ; CC(C)(C)OC(=O)CNC(=O)c1c(O)c2ccc(Br)cc2oc1=O ; O=C(O)CNC(=O)c1c(O)c2ccc(-c3cccnc3)cc2oc1=O]

Similar procedure to the previous example was followed to arrive at the title compound, with the LC-MS [M-H]⁻ m/z 339.

Example 33

Synthesis of N-[(4-hydroxy-2-oxo-7-(pyridin-3-yl)-2H-3-chromenyl)carbonyl]glycine

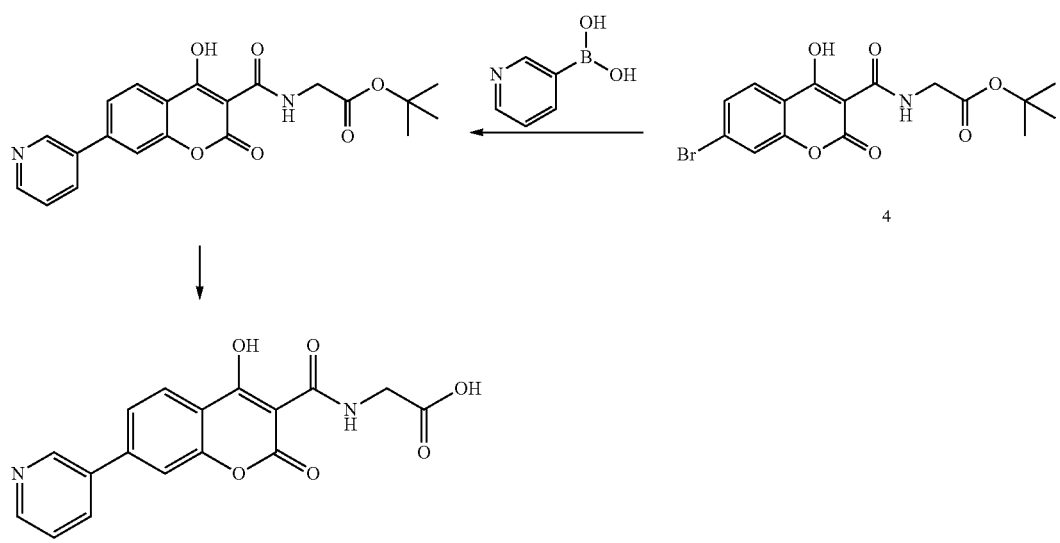

Similar procedure to the previous example was followed to arrive at the title compound, with the LC-MS [M-H]⁻ m/z 339, and $^1$H-NMR (300 MHz, $(CD_3)_2SO$) δ 9.55 (br s, 1H), 9.12 (s, 1H), 8.73 (s, 1H), 8.38 (d, 1H, J=8.1 Hz), 8.11 (d, 1H, J=8.4 Hz), 7.97 (s, 1H), 7.90 (d, 1H, J=8.4 Hz), 7.69-7.65 (m, 1H), 4.16 (d, 2H, J=6.0 Hz).

Example 34

Synthesis of N-[(4-hydroxy-2-oxo-7-phenoxy-2H-3-chromenyl)carbonyl]glycine

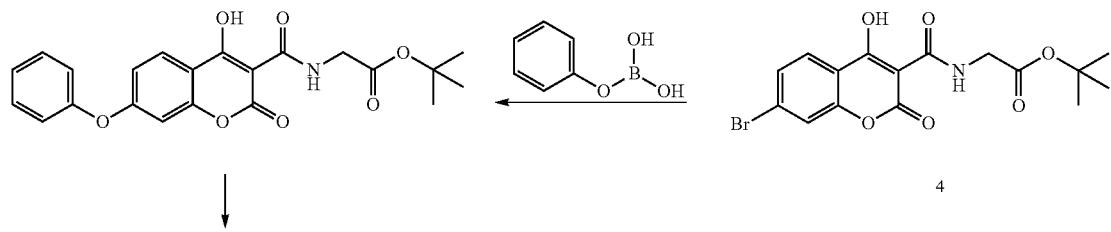

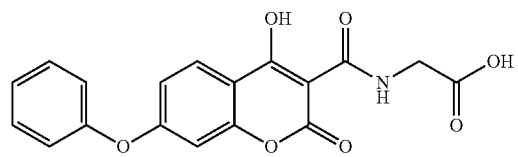

Similar procedure to the previous example was followed to arrive at the title compound, with the LC-MS [M-H]⁻ m/z 354, and ¹H-NMR (300 MHz, (CD$_3$)$_2$SO) δ 9.47 (br s, 1H), 8.99 (d, 1H, 8.7 Hz), 7.55-7.49 (m, 2H), 7.33 (t, 1H, J=7.5 Hz), 7.24-7.21 (m, 2H), 7.05-7.01 (m, 1H), 6.96 (d, 1H, J=2.4 Hz), 4.12 (d, 2H, J=6.0 Hz).

Example 35

Synthesis of N-[(4-hydroxy-2-oxo-7-bromo-3-chromenyl)carbonyl]glycine

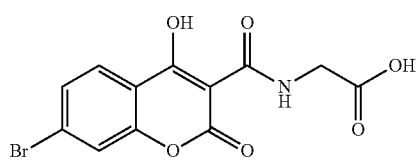 [SMILES: O=C(O)CNC(=O)c1c(O)c2ccc(Br)cc2oc1=O]

Synthesis was shown as of Compound 4 in Example 1, followed by similar procedure to de-protect the t-butyl group on the carboxylate group to arrive at the title compound with the LC-MS [M-H]⁻ m/z 341, and ¹H-NMR (300 MHz, (CD$_3$)$_2$SO) δ 9.53 (br s, 1H), 7.93-7.86 (m, 2H), 7.68-7.65 (m, 1H), 4.14 (m, 2H).

Example 36

Synthesis of N-[(4-hydroxy-2-oxo-8-bromo-3-chromenyl)carbonyl]glycine

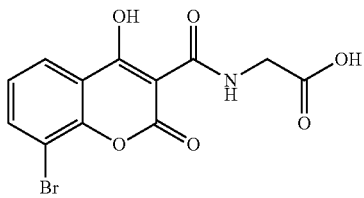 [SMILES: O=C(O)CNC(=O)c1c(O)c2cccc(Br)c2oc1=O]

Synthesis was shown as of Compound 10 in Example 16, followed by similar procedure to de-protect the t-butyl group on the carboxylate group to arrive at the title compound with the LC-MS [M-H]⁻ m/z 341, and ¹H-NMR (300 MHz, (CD$_3$)$_2$SO) δ 9.51 (br s, 1H), 8.12 (d, 1H, J=7.8 Hz), 8.00 (d, 1H, J=7.8 Hz), 7.40 (t, 1H, J=7.8 Hz), 4.15 (d, 2H, J=6.0 Hz).

Example 37

Synthesis of N-[(4-hydroxy-2-oxo-6-bromo-3-chromenyl)carbonyl]glycine

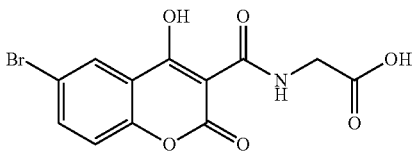 [SMILES: O=C(O)CNC(=O)c1c(O)c2cc(Br)ccc2oc1=O]

Similar procedure to the previous example was followed to arrive at the title compound with the LC-MS [M-H]⁻ m/z 341, and ¹H-NMR (300 MHz, (CD$_3$)$_2$SO) δ 9.56 (br s, 1H), 8.07 (d, 1H, J=2.4 Hz), 7.99 (dd, 1H, J=9.0, 2.4 Hz), 7.49 (d, 1H, J=9.0 Hz), 4.14 (d, 2H, J=6.0 Hz).

Example 38

Synthesis of N-[(4-hydroxy-2-oxo-8-(3-trifluoromethylphenyl)-2H-3-chromenyl)carbonyl]alanine

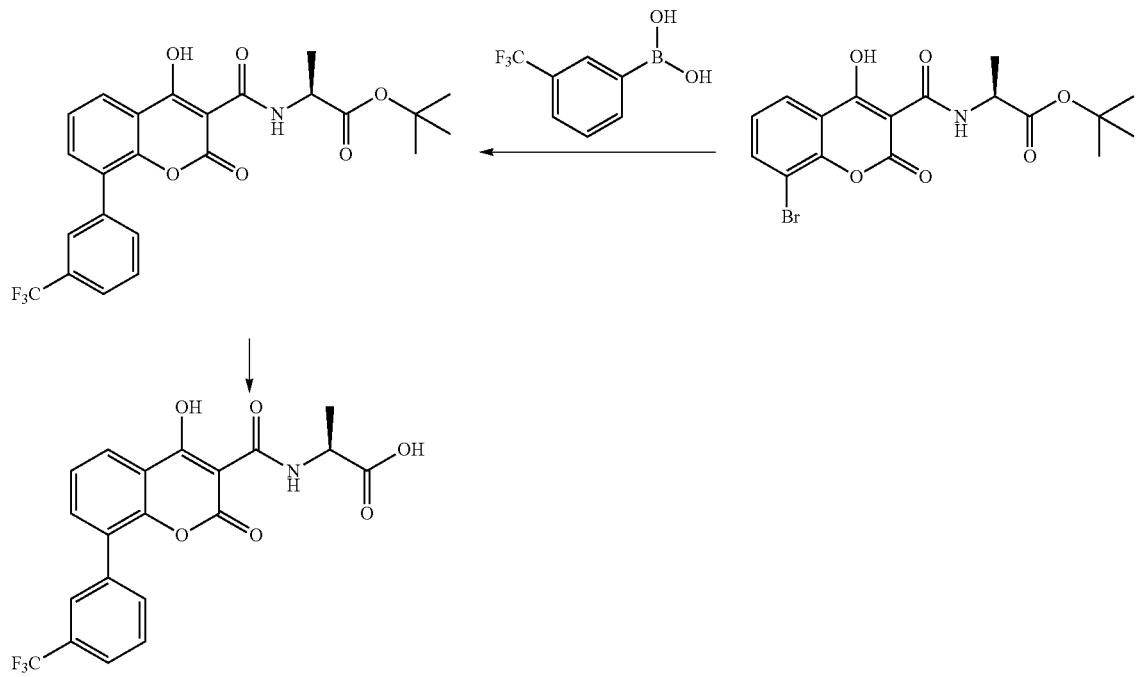

Similar procedure to Example 20 was followed, except that an alanine t-butyl ester was used instead of a glycine t-butyl ester, to arrive at the title compound, with the LC-MS [M-H]$^-$ m/z 420, and $^1$H-NMR (300 MHz, (CD$_3$)$_2$SO) δ 9.59 (br s, 1H), 8.09-8.03 (m, 2H), 7.95 (dd, 2H, J=7.5, 1.5 Hz), 7.86-7.76 (m, 2H), 7.59 (t, 1H, 7.5 Hz), 4.57 (m, 1H), 1.48 (d, 1H, J=7.2 Hz).

Example A

Assay of HIF-PHD2 Enzyme Activity

HIF-PHD2 activity was measured using homogeneous TR-FRET technology (see also, US2008/004817; Dao J H et al., Anal Biochem. 2009, 384:213-23). To each well of a ½Area 96-well plate was added 2 μL of test compound in DMSO and 40 μL of assay buffer (50 mM Tris PH7.4/0.01% Tween-20/0.1 mg/ml BSA/1 mM Sodium ascorbate/20 μg/ml Catalase/10 μM FeSO4) containing 600 nM full length PHD2. After a 30 min preincubation at room temperature, the enzymatic reactions were initiated by the addition of 8 μL of substrates (final concentrations of 0.2 μM 2-oxoglutarate and 0.5 μM HIF-1α peptide biotinyl-DLDLEMLAPYIPMD-DDFQL). After 2 hr at room temperature, the reactions were terminated and signals were developed by the addition of a 50 μL quench/detection mix to a final concentration of 1 mM ortho-phenanthroline, 0.1 mM EDTA, 0.5 nM anti-(His)$_6$ LANCE reagent, 100 nM AF647-labeled Streptavidin, and 30 nM (His)$_6$-VHL-elonginB-elonginC complex. The ratio of time resolved fluorescence signals at 665 and 620 nm was determined, and percent inhibition was calculated relative to an uninhibited control sample run in parallel.

Example B

Determination of Erythropoietin (EPO) Induction in Normal Mice

Eight-week-old male C57BL/6 mice were dosed orally with test compound at 20, 60 and 100 mg/kg. Blood samples were obtained from the orbital venous plexus 6 hours after dosing and serum was collected (see also, Robinson A, et al., Gastroenterology. 2008, 134:145-55; Hsieh M M, et al., Blood. 2007, 110:2140-7). Samples were analyzed for EPO by electrochemiluminescence-based immunoassay (MSD) according to manufacturer's instructions.

Example C

Determination of Hematology in Normal Mice

Eight-week-old male C57BL/6 mice were dosed orally with test compound at 60 mg/kg once a day for a week. Blood samples were obtained from the orbital venous plexus with time points including 1, 3 and 5 days after dosing. An Automated Hematology Analyzer MEK-6318K was used to determine hematological parameters such as erythrocyte counts (RBC), hemoglobin concentration (HGB), hematocrit value (HCT).

Example D

Pharmacokenetics Studies

Test compounds were administered in solution as a single oral dose to fasted male CD (SD) IGS rats (n=6/group) at 50 mg/kg. Plasma samples were obtained from the orbital venous plexus of each individual animal at 15', 30', 1 h, 2 h, 4 h, 6 h, 12 h and 24 h post-administration. Compound blood concentrations in the plasma samples were measured by HPLC.

The $IC_{50}$ values for certain example compounds of invention in the Enzyme Assay of Example A are provided in Table 1 as follows.

TABLE 1

| COMPOUND | Enzyme Assay IC50 (nM) |
|---|---|
| Example 1 | 250 |
| Example 2 | 150 |
| Example 3 | 150 |
| Example 4 | 150 |
| Example 5 | 150 |
| Example 6 | 150 |
| Example 7 | 150 |
| Example 8 | 150 |
| Example 9 | 150 |
| Example 10 | 150 |
| Example 11 | 150 |
| Example 12 | 150 |
| Example 13 | 150 |
| Example 14 | 300 |
| Example 15 | 150 |
| Example 16 | 350 |
| Example 17 | 200 |
| Example 18 | 90 |
| Example 19 | 150 |
| Example 20 | 100 |
| Example 21 | 90 |
| Example 22 | 100 |
| Example 23 | 150 |
| Example 24 | 30 |
| Example 25 | 150 |
| Example 26 | 150 |
| Example 27 | 150 |
| Example 28 | 80 |
| Example 29 | 150 |
| Example 30 | 80 |
| Example 31 | — |
| Example 32 | — |
| Example 33 | 200 |
| Example 34 | 150 |
| Example 35 | 150 |
| Example 36 | 300 |
| Example 37 | 700 |
| Example 38 | — |

Although the present invention has been described in considerable detail with reference to certain preferred versions thereof, other versions are possible. Therefore, the spirit and scope of the invention should not be limited to the description of the preferred versions described herein.

All features disclosed in the specification, including the abstract and drawings, and all the steps in any method or process disclosed, may be combined in any combination, except combinations where at least some of such features and/or steps are mutually exclusive. Each feature disclosed in the specification, including abstract and drawings, can be replaced by alternative features serving the same, equivalent or similar purpose, unless expressly stated otherwise. Thus, unless expressly stated otherwise, each feature disclosed is one example only of a generic series of equivalent or similar features. Various modifications of the invention, in addition to those described herein, will be apparent to those skilled in the art from the foregoing description. Such modifications are also intended to fall within the scope of the appended claims.

Each reference cited in the present application is herein incorporated by reference in its entirety.

What is claimed is:

1. A compound of Formula I:

or a pharmaceutically acceptable salt thereof, wherein:
n is 1;
$R_1$ is OH;
$R_2$ and $R_3$ are each H;
$R_4$ is H or unsubstituted alkyl;
$R_5$ is OH or lower alkoxy;
$R_6$ and $R_7$ are each H;
$R_8$ is heteroaryl, substituted heteroaryl, phenyl or phenyl substituted by halogen alkyl, alkoxy, haloalkyl, or haloalkoxy and $R_9$ is H; or $R_8$ is H and $R_9$ is substituted phenyl.

2. The compound of claim 1, wherein $R_3$ and $R_4$ are each H.

3. The compound of claim 1, wherein $R_5$ is OH.

4. The compound of claim 1, wherein at least one of $R_8$ and $R_9$ is halo or a moiety substituted with at least one halo.

5. The compound of claim 1, wherein at least one of $R_8$ and $R_9$ is aryl, substituted aryl, heteroaryl, substituted heteroaryl, heterocycloalkyl, and substituted heterocycloalkyl.

6. The compound of claim 1, wherein at least one of $R_8$ and $R_9$ is substituted aryl, or substituted heteroaryl.

7. The compound of claim 1, wherein at least one of $R_8$ and $R_9$ is substituted phenyl or substituted pyridyl.

8. The compound of claim 1, wherein at least one of $R_8$ and $R_9$ is phenyl and substituted with halogen, alkyl, haloalkyl, alkoxy, or haloalkoxy at the para- and/or meta-position.

9. The compound of claim 1, wherein $R_8$ is pyridyl substituted with halogen, alkyl, haloalkyl, alkoxy, or haloalkoxy at the para- and/or meta-position.

10. The compound of claim 1, wherein the compound is of Formula II:

wherein:
$R^{21}$ is H, halogen, lower alkyl, lower haloalkyl, lower alkoxy, or lower haloalkoxy;
$R^{22}$ is H, halogen, lower alkyl, lower haloalkyl, lower alkoxy, or lower haloalkoxy;
$Z^1$ is $CR^{23}$; and $R^{23}$ is H, halogen, lower alkyl, lower haloalkyl, lower alkoxy, or lower haloalkoxy;

provided that at least one of $R^{21}$ and $R^{22}$ and $R^{23}$ (if present) is halogen, lower alkyl, lower haloalkyl, lower alkoxy, or lower haloalkoxy.

11. The compound of claim 10, wherein each of $R^{21}$, $R^{22}$, and $R^{23}$ (if present) is independently H, Cl, F, methyl, ethyl, trifluoromethyl, methoxy, ethoxy, or trifluoromethoxy.

12. The compound of claim 10, wherein one of $R^{21}$, $R^{22}$, and $R^{23}$ is halogen, lower alkyl, lower haloalkyl, lower alkoxy, or lower haloalkoxy; and the other two of $R^{21}$, $R^{22}$, and $R^{23}$ are both H.

13. The compound of claim 10, wherein one of $R^{21}$ and $R^{23}$ is halogen, lower alkyl, lower haloalkyl, lower alkoxy, or lower haloalkoxy; and the other one of $R^{21}$ and $R^{23}$ is H; $R^{22}$ is H.

14. The compound of claim 10, wherein two of $R^{21}$, $R^{22}$, and $R^{23}$ are each independently halogen, lower alkyl, lower haloalkyl, lower alkoxy, and lower haloalkoxy; and the other one of $R^{21}$, $R^{22}$, and $R^{23}$ is H.

15. The compound of claim 10, wherein $R^{21}$, $R^{22}$, and $R^{23}$ are each independently halogen, lower alkyl, lower haloalkyl, lower alkoxy, or lower haloalkoxy.

16. The compound of claim 10, wherein the compound is of Formula IIa:

wherein:
$R^{21}$ is H, halogen, lower alkyl, lower haloalkyl, lower alkoxy, or lower haloalkoxy; and
$R^{22}$ is H, halogen, lower alkyl, lower haloalkyl, lower alkoxy, or lower haloalkoxy;
provided that at least one of $R^{21}$ and $R^{22}$ is halogen, lower alkyl, lower haloalkyl, lower alkoxy, or lower haloalkoxy.

17. The compound claim 16, wherein $R^{21}$ is H; and $R^{22}$ is lower alkyl or lower haloalkyl.

18. The compound of claim 16, wherein $R^{21}$ is H; and $R^{22}$ is $C_{1-3}$ alkyl or $C_{1-3}$ haloalkyl.

19. The compound of claim 18, wherein $R^{22}$ is methyl or $C_{1-2}$ haloalkyl.

20. The compound of claim 18, wherein $R^{22}$ is methyl or ethyl.

21. The compound of claim 16, wherein $R^{22}$ is H; and $R^{21}$ is lower alkyl or lower haloalkyl.

22. The compound of claim 16, wherein $R^{21}$ and $R^{22}$ are each independently halogen, lower alkyl, lower haloalkyl, lower alkoxy, or lower haloalkoxy.

23. The compound of claim 16, wherein $R^{21}$ is methyl or ethyl.

24. The compound of claim 16, wherein $R^{21}$ is methyl or $C_{1-2}$ haloalkyl.

25. The compound of claim 16, wherein $R^{21}$ and $R^{22}$ are each independently $C_{1-2}$ alkyl or $C_{1-2}$ haloalkyl.

26. The compound of claim 1, wherein the compound of Formula III:

wherein:
$R^{24}$; and $R^{25}$ are each independently H, halogen, lower alkyl, lower haloalkyl, lower alkoxy, or lower haloalkoxy;
$Z^2$ is N or $CR^{26}$; and
$R^{26}$ is H, halogen, lower alkyl, lower haloalkyl, lower alkoxy, or lower haloalkoxy;
provided that at least one of $R^{24}$ and $R^{25}$ and $R^{26}$ (if present) is halogen, lower alkyl, lower haloalkyl, lower alkoxy, or lower haloalkoxy.

27. The compound of claim 26, wherein $Z^2$ is $CR^{26}$.

28. The compound of claim 26, wherein each of $R^{24}$, $R^{25}$, and $R^{26}$ (if present) is H, Cl, F, methyl, ethyl, trifluoromethyl, methoxy, ethoxy, or trifluoromethoxy.

29. The compound of claim 26, wherein $Z^2$ is $CR^{26}$; one of $R^{24}$, $R^{25}$, and $R^{26}$ is halogen, lower alkyl, lower haloalkyl, lower alkoxy, or lower haloalkoxy; and the other two of $R^{24}$, $R^{25}$, and $R^{26}$ are both H.

30. The compound of claim 26, wherein $Z^2$ is $CR^{26}$; one of $R^{24}$ and $R^{26}$ is halogen, lower alkyl, lower haloalkyl, lower alkoxy, or lower haloalkoxy; and the other one of $R^{24}$ and $R^{26}$ is H; and $R^{25}$ is H.

31. The compound of claim 26, wherein $Z^1$ is $CR^{26}$; two of $R^{24}$, $R^{25}$, and $R^{26}$ are each independently halogen, lower alkyl, lower haloalkyl, lower alkoxy, or lower haloalkoxy; and the other one of $R^{24}$, $R^{25}$, and $R^{26}$ is H.

32. The compound of claim 26, wherein $Z^2$ is $CR^{26}$; $R^{24}$, $R^{25}$, and $R^{26}$ are each independently halogen, lower alkyl, lower haloalkyl, lower alkoxy, or lower haloalkoxy.

33. The compound of claim 26, wherein $Z^2$ is N.

34. The compound of claim 26, wherein $Z^2$ is N; one of $R^{24}$ and $R^{25}$ is halogen, lower alkyl, lower haloalkyl, lower alkoxy, or lower haloalkoxy; and the other of $R^{24}$ and $R^{25}$ is H.

35. The compound of claim 26, wherein the compound is of Formula IIIa wherein:
$R^{24}$ is H, halogen, lower alkyl, lower haloalkyl, lower alkoxy, or lower haloalkoxy; and $R^{25}$ is H, halogen, lower alkyl, lower haloalkyl, lower alkoxy, or lower haloalkoxy;

provided that at least one of $R^{24}$ and $R^{25}$ is halogen, lower alkyl, lower haloalkyl, lower alkoxy, or lower haloalkoxy.

36. The compound of claim 35, wherein $R^{24}$ is H; and $R^{25}$ is lower alkyl or lower haloalkyl.

37. The compound of claim 35, wherein $R^{24}$ is H; and $R^{25}$ is $C_{1-3}$ alkyl or $C_{1-3}$ haloalkyl.

38. The compound of claim 37, wherein $R^{25}$ is methyl and $C_{1-2}$ haloalkyl.

39. The compound of claim 37, wherein $R^{25}$ is methyl or ethyl.

40. The compound of claim 35, wherein $R^{25}$ is lower alkyl or lower haloalkyl.

41. The compound of claim 35, wherein $R^{24}$ is methyl or $C_{1-2}$ haloalkyl.

42. The compound of claim 35, wherein $R^{24}$ is methyl or ethyl.

43. The compound of claim 35, wherein $R^{24}$ and $R^{25}$ are each independently halogen, lower alkyl, lower haloalkyl, lower alkoxy, or lower haloalkoxy.

44. The compound of claim 35, wherein $R^{24}$ and $R^{25}$ are each independently $C_{1-2}$ alkyl or $C_{1-2}$ haloalkyl.

45. The compound of claim 1, wherein the compound is:
2-(4-hydroxy-2-oxo-7-phenyl-2H-chromene-3-carboxamido)acetic acid;
2-(7-(2-chlorophenyl)-4-hydroxy-2-oxo-2H-chromene-3-carboxamido)acetic acid;
2-(7-(3-chlorophenyl)-4-hydroxy-2-oxo-2H-chromene-3-carboxamido)acetic acid;
2-(7-(4-chlorophenyl)-4-hydroxy-2-oxo-2H-chromene-3-carboxamido)acetic acid;
2-(4-hydroxy-2-oxo-7-(3-(trifluoromethyl)phenyl)-2H-chromene-3-carboxamido)acetic acid;
2-(4-hydroxy-2-oxo-7-(4-(trifluoromethyl)phenyl)-2H-chromene-3-carboxamido)acetic acid;
2-(4-hydroxy-2-oxo-7-(3-(trifluoromethoxy)phenyl)-2H-chromene-3-carboxamido)acetic acid;
2-(4-hydroxy-2-oxo-7-(4-(trifluoromethoxy)phenyl)-2H-chromene-3-carboxamido)acetic acid;
2-(7-(3,4-dichlorophenyl)-4-hydroxy-2-oxo-2H-chromene-3-carboxamido)acetic acid;
2-(7-(3,4-difluorophenyl)-4-hydroxy-2-oxo-2H-chromene-3-carboxamido)acetic acid;
2-(4-hydroxy-2-oxo-7-(3,4,5-trifluorophenyl)-2H-chromene-3-carboxamido)acetic acid;
2-(4-hydroxy-7-(3-methoxyphenyl)-2-oxo-2H-chromene-3-carboxamido)acetic acid;
2-(4-hydroxy-7-(4-methoxyphenyl)-2-oxo-2H-chromene-3-carboxamido)acetic acid;
2-(4-hydroxy-2-oxo-7-m-tolyl-2H-chromene-3-carboxamido)acetic acid;
2-(4-hydroxy-2-oxo-7-p-tolyl-2H-chromene-3-carboxamido)acetic acid;
2-(8-(2-chlorophenyl)-4-hydroxy-2-oxo-2H-chromene-3-carboxamido)acetic acid;
2-(8-(3-chlorophenyl)-4-hydroxy-2-oxo-2H-chromene-3-carboxamido)acetic acid;
2-(8-(4-chlorophenyl)-4-hydroxy-2-oxo-2H-chromene-3-carboxamido)acetic acid;
2-(4-hydroxy-2-oxo-8-(3-(trifluoromethyl)phenyl)-2H-chromene-3-carboxamido)acetic acid;
2-(4-hydroxy-2-oxo-8-(4-(trifluoromethyl)phenyl)-2H-chromene-3-carboxamido)acetic acid;
2-(4-hydroxy-2-oxo-8-(3-(trifluoromethoxy)phenyl)-2H-chromene-3-carboxamido)acetic acid;
2-(4-hydroxy-2-oxo-8-(4-(trifluoromethoxy)phenyl)-2H-chromene-3-carboxamido)acetic acid;
2-(8-(3,4-dichlorophenyl)-4-hydroxy-2-oxo-2H-chromene-3-carboxamido)acetic acid;
2-(8-(3,4-difluorophenyl)-4-hydroxy-2-oxo-2H-chromene-3-carboxamido)acetic acid;
2-(4-hydroxy-2-oxo-8-(3,4,5-trifluorophenyl)-2H-chromene-3-carboxamido)acetic acid;
2-(4-hydroxy-8-(3-methoxyphenyl)-2-oxo-2H-chromene-3-carboxamido)acetic acid;
2-(4-hydroxy-8-(4-methoxyphenyl)-2-oxo-2H-chromene-3-carboxamido)acetic acid;
2-(4-hydroxy-2-oxo-8-m-tolyl-2H-chromene-3-carboxamido)acetic acid;
2-(4-hydroxy-2-oxo-8-p-tolyl-2H-chromene-3-carboxamido)acetic acid;
2-(4-hydroxy-7-(6-methoxypyridin-3-yl)-2-oxo-2H-chromene-3-carboxamido)acetic acid;
2-(4-hydroxy-2-oxo-7-(pyridin-4-yl)-2H-chromene-3-carboxamido)acetic acid;
2-(4-hydroxy-2-oxo-7-(pyridin-3-yl)-2H-chromene-3-carboxamido)acetic acid;
or
2-(4-hydroxy-2-oxo-8-(3-(trifluoromethyl)phenyl)-2H-chromene-3-carboxamido)acetic acid.

46. A pharmaceutical composition comprising at least one pharmaceutically acceptable excipient, adjuvant or carrier, and a therapeutically effective amount of a compound of claim 1.

47. The pharmaceutical composition of claim 46, wherein the compound of claim 1 is:
2-(4-hydroxy-2-oxo-7-phenyl-2H-chromene-3-carboxamido)acetic acid;
2-(7-(2-chlorophenyl)-4-hydroxy-2-oxo-2H-chromene-3-carboxamido)acetic acid;
2-(7-(3-chlorophenyl)-4-hydroxy-2-oxo-2H-chromene-3-carboxamido)acetic acid;
2-(7-(4-chlorophenyl)-4-hydroxy-2-oxo-2H-chromene-3-carboxamido)acetic acid;
2-(4-hydroxy-2-oxo-7-(3-(trifluoromethyl)phenyl)-2H-chromene-3-carboxamido)acetic acid;
2-(4-hydroxy-2-oxo-7-(4-(trifluoromethyl)phenyl)-2H-chromene-3-carboxamido)acetic acid;
2-(4-hydroxy-2-oxo-7-(3-(trifluoromethoxy)phenyl)-2H-chromene-3-carboxamido)acetic acid;
2-(4-hydroxy-2-oxo-7-(4-(trifluoromethoxy)phenyl)-2H-chromene-3-carboxamido)acetic acid;
2-(7-(3,4-dichlorophenyl)-4-hydroxy-2-oxo-2H-chromene-3-carboxamido)acetic acid;
2-(7-(3,4-difluorophenyl)-4-hydroxy-2-oxo-2H-chromene-3-carboxamido)acetic acid;
2-(4-hydroxy-2-oxo-7-(3,4,5-trifluorophenyl)-2H-chromene-3-carboxamido)acetic acid;
2-(4-hydroxy-7-(3-methoxyphenyl)-2-oxo-2H-chromene-3-carboxamido)acetic acid;
2-(4-hydroxy-7-(4-methoxyphenyl)-2-oxo-2H-chromene-3-carboxamido)acetic acid;
2-(4-hydroxy-2-oxo-7-m-tolyl-2H-chromene-3-carboxamido)acetic acid;
2-(4-hydroxy-2-oxo-7-p-tolyl-2H-chromene-3-carboxamido)acetic acid;
2-(8-(2-chlorophenyl)-4-hydroxy-2-oxo-2H-chromene-3-carboxamido)acetic acid;
2-(8-(3-chlorophenyl)-4-hydroxy-2-oxo-2H-chromene-3-carboxamido)acetic acid;
2-(8-(4-chlorophenyl)-4-hydroxy-2-oxo-2H-chromene-3-carboxamido)acetic acid;
2-(4-hydroxy-2-oxo-8-(3-(trifluoromethyl)phenyl)-2H-chromene-3-carboxamido)acetic acid;

2-(4-hydroxy-2-oxo-8-(4-(trifluoromethyl)phenyl)-2H-chromene-3-carboxamido)acetic acid;

2-(4-hydroxy-2-oxo-8-(3-(trifluoromethoxy)phenyl)-2H-chromene-3-carboxamido)acetic acid;

2-(4-hydroxy-2-oxo-8-(4-(trifluoromethoxy)phenyl)-2H-chromene-3-carboxamido)acetic acid;

2-(8-(3,4-dichlorophenyl)-4-hydroxy-2-oxo-2H-chromene-3-carboxamido)acetic acid;

2-(8-(3,4-difluorophenyl)-4-hydroxy-2-oxo-2H-chromene-3-carboxamido)acetic acid;

2-(4-hydroxy-2-oxo-8-(3,4,5-trifluorophenyl)-2H-chromene-3-carboxamido)acetic acid;

2-(4-hydroxy-8-(3-methoxyphenyl)-2-oxo-2H-chromene-3-carboxamido)acetic acid;

2-(4-hydroxy-8-(4-methoxyphenyl)-2-oxo-2H-chromene-3-carboxamido)acetic acid;

2-(4-hydroxy-2-oxo-8-m-tolyl-2H-chromene-3-carboxamido)acetic acid;

2-(4-hydroxy-2-oxo-8-p-tolyl-2H-chromene-3-carboxamido)acetic acid;

2-(4-hydroxy-7-(6-methoxypyridin-3-yl)-2-oxo-2H-chromene-3-carboxamido)acetic acid;

2-(4-hydroxy-2-oxo-7-(pyridin-4-yl)-2H-chromene-3-carboxamido)acetic acid;

2-(4-hydroxy-2-oxo-7-(pyridin-3-yl)-2H-chromene-3-carboxamido)acetic acid;

or 2-(4-hydroxy-2-oxo-8-(3-(trifluoromethyl)phenyl)-2H-chromene-3-carboxamido)acetic acid.

48. The pharmaceutical composition of claim 46, further comprising an erythropoiesis stimulating agent or a chemotherapeutic agent.

49. The pharmaceutical composition of claim 46, wherein the compound of claim 1 is present in an amount effective for the treatment of diabetes, cancer, ischemia, anemia, or thalassemia.

* * * * *